United States Patent
Griffin et al.

(10) Patent No.: US 12,220,500 B2
(45) Date of Patent: Feb. 11, 2025

(54) COMPOSITIONS AND METHODS FOR PREPARING AND USING NON-IMMUNOGENIC FAST ANNEALING MICROPOROUS ANNEALED PARTICLE HYDROGELS

(71) Applicant: University of Virginia Patent Foundation, Charlottesville, VA (US)

(72) Inventors: Donald Richieri Griffin, Charlottesville, VA (US); James J. Daniero, Charlottesville, VA (US); Lauren Jae Pruett, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 924 days.

(21) Appl. No.: 17/044,058

(22) PCT Filed: Apr. 15, 2019

(86) PCT No.: PCT/US2019/027509
§ 371 (c)(1),
(2) Date: Sep. 30, 2020

(87) PCT Pub. No.: WO2019/200390
PCT Pub. Date: Oct. 17, 2019

(65) Prior Publication Data
US 2021/0052779 A1    Feb. 25, 2021

Related U.S. Application Data

(60) Provisional application No. 62/657,015, filed on Apr. 13, 2018.

(51) Int. Cl.
| | | |
|---|---|---|
| *A61L 27/52* | (2006.01) | |
| *A61L 27/36* | (2006.01) | |
| *A61L 27/48* | (2006.01) | |
| *A61L 27/54* | (2006.01) | |
| *A61L 27/56* | (2006.01) | |
| *C08L 33/26* | (2006.01) | |
| *C08L 71/02* | (2006.01) | |

(52) U.S. Cl.
CPC .......... *A61L 27/52* (2013.01); *A61L 27/3679* (2013.01); *A61L 27/48* (2013.01); *A61L 27/54* (2013.01); *A61L 27/56* (2013.01); *C08L 33/26* (2013.01); *C08L 71/02* (2013.01); *A61L 2300/236* (2013.01); *A61L 2400/06* (2013.01); *A61L 2400/18* (2013.01)

(58) Field of Classification Search
CPC ...... A61L 27/52; A61L 27/3679; A61L 27/48; A61L 27/54; A61L 27/56; A61L 2300/236; A61L 2400/06; A61L 2400/18; C08L 33/26; C08L 71/02
See application file for complete search history.

(56) References Cited

U.S. PATENT DOCUMENTS

| | | | | |
|---|---|---|---|---|
| 2003/0059474 A1* | 3/2003 | Scott | ................... | A61K 9/1635 424/491 |
| 2006/0292198 A1* | 12/2006 | Dalal | ..................... | A61L 27/50 424/602 |
| 2006/0292199 A1 | 12/2006 | Kuhn et al. | | |
| 2010/0055184 A1 | 3/2010 | Zeitels | | |
| 2010/0316724 A1* | 12/2010 | Whitfield | ............. | A61K 9/1694 424/278.1 |
| 2015/0031638 A1* | 1/2015 | Ekre | ...................... | A61P 33/06 514/25 |
| 2016/0279283 A1 | 9/2016 | Griffin et al. | | |
| 2020/0306413 A1 | 10/2020 | Di Carlo et al. | | |

FOREIGN PATENT DOCUMENTS

| | | |
|---|---|---|
| EP | 3773770 | 2/2021 |
| WO | WO2013/049404 | 4/2013 |
| WO | WO2017/142879 | 8/2017 |
| WO | WO2017/177225 | 10/2017 |

OTHER PUBLICATIONS

Griffin et al., "Accelerated wound healing by injectable microporous gel scaffolds assembled from annealed building blocks" in nature materials, vol. 14, Jul. 2015. (Year: 2015).*

Griffin et al, "Accelerated wound healing by injectable microporous gel scaffolds assembled from annealed building blocks" vol. 14, HHS Access, Jul. 2015. (Year: 2015).*

Fry et al., "Synthesis and anticoagulant activity of heparin immobilized "end-on" to polystyrene microspheres coated with end-group activated polyethylene oxide" in 2010 Wiley Periodicals. (Year: 2010).*

Alipour et al. Phonatory characteristics of the excised human larynx in comparison to other species J Voice. Jul. 2013;27(4):441-7. doi: 10.1016/j.jvoice.2013.03.013.

Communication corresponding to Canadian Patent Office corresponding to Application No. PCT/US2019/027509 dated Nov. 2, 2020.

(Continued)

*Primary Examiner* — Blessing M Fubara

(57) ABSTRACT

Non-degradable, non-immunogenic microporous hydrogel compositions are provided. Such hydrogel compositions consist of flowable hydrogel particles comprising a bioinert polymeric backbone, including for example a poly(ethylene glycol)(PEG)-based polymeric backbone, an annealing component comprising a physiologically-stable, radically polymerizable alkene, including for example methacrylamide, and a heparin compound. Methods of treating glottic incompetence and/or providing laryngeal reconstruction are also provided. Such methods consist of providing a subject suffering from glottic incompetence and/or in need of laryngeal reconstruction, and administering a non-degradable, non-immunogenic microporous hydrogel composition disclosed herein.

19 Claims, 12 Drawing Sheets

(56) References Cited

OTHER PUBLICATIONS

Communication corresponding to European Patent office corresponding to Application No. 19785859 dated Dec. 3, 2021.
Communication corresponding to European Patent office corresponding to Application No. 19785859 dated Jan. 20, 2021.
Communication from the European Patent office corresponding to Application No. 19785859 dated Oct. 24, 2022.
Dion et al. Functional assessment of the ex vivo vocal folds through biomechanical testing: A review. Mater Sci Eng C Mater Biol Appl. Jul. 1, 2016;64:444-453. doi: 10.1016/j.msec.2016.04.018.
Extended European Search Report corresponding to European Patent Application No. 19785859.0 dated Dec. 3, 2021.
International Preliminary Report on Patentability corresponding to International Application No. PCT/US2019/027509 dated Oct. 13, 2020.
International Search Report corresponding to International Application No. PCT/US2019/027509 dated Jul. 1, 2019.
Office Action corresponding to Israeli Patent Application No. 278012 dated May 31, 2021.
Office Action corresponding to the Israeli Patent Office corresponding to Application No. 278012 dated Jan. 26, 2022.
Written Opinion corresponding to International Application No. PCT/US2019/027509 dated Oct. 17, 2019.
First Examination report received in Israeli Patent Application No. 278012 mailed on May 8, 2023, 17 pages.
Office Action (Decision to Grant) corresponding to European Patent Application No. 19785859 dated Nov. 3, 2023, 2 pages.
Office Action (Intention to Grant) corresponding to European Patent Application No. 19785859 dated Jun. 21, 2023, 172 pages.

* cited by examiner

FIG. 5A
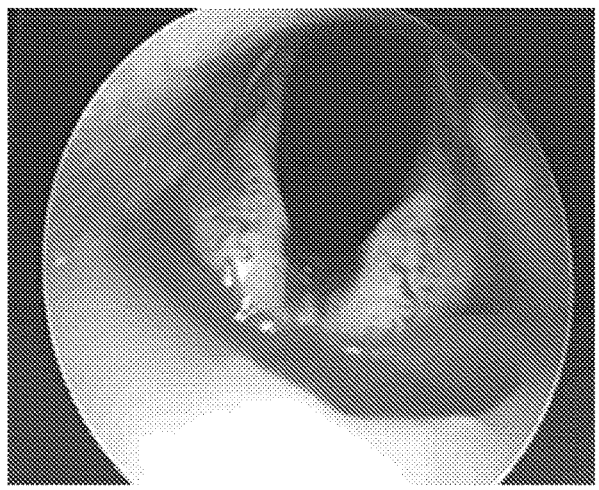 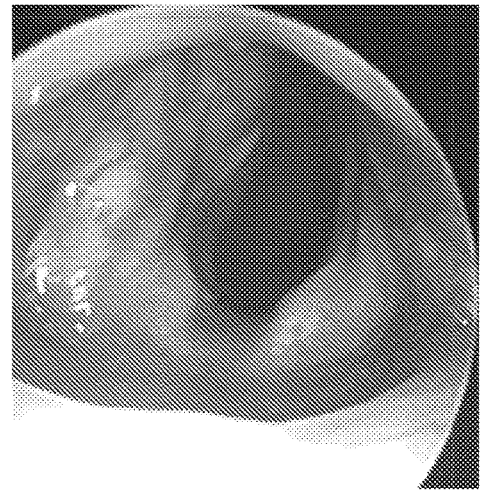
FIG. 5B    FIG. 5C

COMPOSITIONS AND METHODS FOR PREPARING AND USING NON-IMMUNOGENIC FAST ANNEALING MICROPOROUS ANNEALED PARTICLE HYDROGELS

CROSS-REFERENCE TO RELATED APPLICATIONS

This application claims benefit of U.S. Provisional Patent Application Ser. No. 62/657,015, filed Apr. 13, 2018, herein incorporated by reference in its entirety.

TECHNICAL FIELD

The subject matter disclosed herein relates generally to compositions and methods for preparing and using non-immunogenic fast annealing microporous annealed particle hydrogels. More specifically, disclosed herein are injectable non-degradable, non-immunogenic microporous hydrogel composition for treating various conditions, including glottic incompetence.

BACKGROUND

Glottic incompetence is a common laryngeal disorder that can cause loss of voice (dysphonia) and swallowing function (dysphagia), which significantly lowers an individual's quality of life. Causes of glottic incompetence include vocal fold atrophy, paralysis, scar, and tissue loss from surgery or radiation therapy. Currently, the treatment is either through medialization of the impaired vocal fold with injectable fillers (temporary) or surgical manipulation of the laryngeal framework (permanent). Injectable methods are preferred, when appropriate, because they reduce hours of inpatient surgery to a brief outpatient visit, significantly reducing health care expenditures and improving patient recovery experience. Over 7,000 vocal fold injections were performed in the Medicare population alone during 2012 and initial treatment with an office-based injectable method results in significant cost savings over surgical alternatives. The difficulty with current methods is that they rely on natural polymers, which provide good integration but sacrifice longevity (only last 1-18 months) and often require long-term surgical correction. What is needed is a composition, such as an injectable filler, that provides integration and is substantially or completely non-resorbable and/or non-degradable.

The need for suitable dermal fillers for other applications and therapies is also needed. For example, a need exists for dermal fillers for conditions requiring tissue bulking, including for example, but not limited to, treatment of post-myocardial infarction scarring, facial augmentation and rejuvenation, and treatment of arthritis. For such applications what is needed is a composition, such as an injectable filler, that provides integration and is non-resorbable and/or non-degradable.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are non-degradable, non-immunogenic microporous hydrogel compositions that comprise a collection of flowable hydrogel particles comprising a bioinert polymeric backbone, an annealing component comprising a physiologically-stable, radically polymerizable alkene, wherein the annealing component links the flowable hydrogel particles, and a heparin compound. The microporous hydrogel composition can be substantially non-degradable and substantially non-immunogenic. In some aspects, the bioinert polymeric backbone can comprises a poly(ethylene glycol)(PEG), and the physiologically-stable, radically polymerizable alkene can comprise a methacrylamide.

In some embodiments, the heparin compound can be heterogeneously distributed throughout the microporous hydrogel composition. In some embodiments, the heparin compound can be unevenly distributed throughout the microporous hydrogel composition to thereby form heparin islands, comprising single or clustered groups of microgels, isolated within the microporous hydrogel composition.

In some aspects, such non-immunogenic microporous hydrogel composition can comprise a synthesized 4-armed PEG, optionally wherein approximately 1 to 2 arms of the 4-armed PEG comprise a maleimide functional group, and wherein approximately 2 to 3 arms of the 4-armed PEG comprise a methacrylamide functional group.

Such compositions can further comprise an annealing initiator, wherein activation of the annealing initiator can cause annealing of the flowable hydrogel particles to form a scaffold of hydrogel particles having interstitial spaces therein.

The substantially non-degradable microporous hydrogel can be configured to resist degradation in vivo for at least 90 days, preferably at least 180 days, most preferably indefinitely. Furthermore, such compositions can be configured such that less than about 40% of cells present within the microporous hydrogel composition following 6 months in vivo are immune cells.

In some embodiments, provided herein are methods of treating a tissue comprising, delivering to the tissue a non-degradable, non-immunogenic microporous hydrogel composition as disclosed herein, and activating an annealing initiator to thereby anneal the flowable hydrogel particles to form a covalently-stabilized scaffold of hydrogel particles. In some embodiments, exposing the non-degradable, non-immunogenic microporous hydrogel composition to an annealing initiator can comprise exposing the microporous hydrogel to a light source or a heat source. In some aspects, the tissue to be treated can comprise a laryngeal vocal fold, superficial lamina propria and/or vocalis muscle. The laryngeal vocal fold can be in a subject suffering from glottic incompetence and/or a subject in need of laryngeal reconstruction In some embodiments, the non-degradable, non-immunogenic microporous hydrogel composition can be configured to resist degradation in vivo for at least 90 days, preferably at least 180 days, most preferably indefinitely. Moreover, when administered, due to its low immunogenicity, less than about 40% of cells present within the microporous hydrogel composition following 6 months in vivo are immune cells. Still yet, administration of the microporous hydrogel composition with a heterogeneously distributed heparin compound can in some aspects cause increased tissue infiltration and vascularization with no substantial difference in immune response as compared to a microporous hydrogel composition without a heterogeneously distributed heparin compound.

In some embodiments, provided herein are methods of treating glottic incompetence, including providing a subject suffering from glottic incompetence and/or in need of laryngeal reconstruction, and administering a non-degradable, non-immunogenic microporous hydrogel composition disclosed herein to a laryngeal vocal fold and/or vocalis muscle, whereby the glottic incompetence in treated.

These and other objects are achieved in whole or in part by the presently disclosed subject matter. Further, objects of the presently disclosed subject matter having been stated above, other objects and advantages of the presently disclosed subject matter will become apparent to those skilled in the art after a study of the following description, drawings and examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter.

For a more complete understanding of the presently disclosed subject matter, reference is now made to the following drawings in which:

FIGS. 2A through 2E depict images of the disclosed hydrogel compositions and approaches for making the same, wherein FIG. 2A depicts a series of electromicrographs of a three-dimensional scaffolds of annealed hydrogel particles, FIG. 2B is a schematic depicting the components of a disclosed hydrogel compositions and approaches for making the same, and FIGS. 2C through 2E are images of disclosed hydrogel compositions, including the formation of microparticles (FIG. 2D) and nanoparticles (FIG. 2E);

FIGS. 5A through 5D illustrate the successful injection augmentation and annealing in a leporine (rabbit) model (photograph—FIG. 5A), with endoscopic images of the larynx shown in FIGS. 5B and 5C and an H&E slide of the left hemilarynx in FIG. 5D;

FIG. 7D shows early vascularization using CD31$^+$ fluorescent imaging within the tissue only 6 weeks after injection (left panel; right panel is saline control at 6 months)

DETAILED DESCRIPTION

Figure 1A:
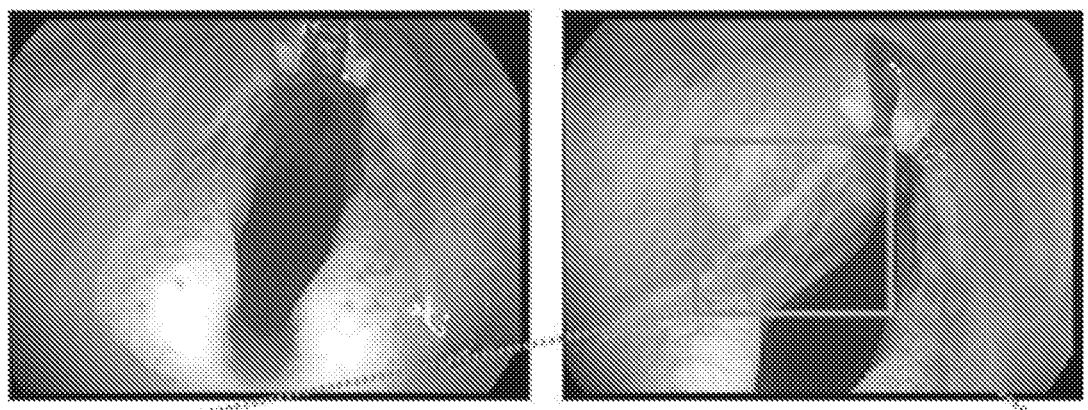
FIGS. 1A and 1B illustrate glottic incompetence in a subject (FIG. 1A) and a hydrogel composition for treatment of the same (FIG. 1B), with FIG. 1A showing photographs of vocal folds in a leporine model pre-medialization (left panel) and post-medialization (right panel), and a schematic of disclosed hydrogel compositions used for vocal fold medialization in FIG. 1B.

The presently disclosed subject matter now will be described more fully hereinafter, in which some, but not all embodiments of the presently disclosed subject matter are described. Indeed, the disclosed subject matter can be embodied in many different forms and should not be construed as limited to the embodiments set forth herein; rather, these embodiments are provided so that this disclosure will satisfy applicable legal requirements.

Abbreviations and Acronyms

GRAS—Generally Regarded As Safe
MAP—microporous annealed particle
PCL—polycaprolactone
PDGF—platelet derived growth factor
PEG—poly(ethylene glycol)
PLA—poly(lactic acid)
PLAGA—poly(lactic-co-glycolic acid; also referred to as poly(lactide-co-glycolide) and poly (D, L-lactic-co-glycolic acid
PLA/PEO—poly(lactic acid)-poly(ethylene oxide)
PLGA—poly(lactide-co-glycolide)

General Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one skilled in the art. While the following terms are believed to be well understood by one of ordinary skill in the art, the following definitions are set forth to facilitate explanation of the presently disclosed subject matter.

In describing the presently disclosed subject matter, it will be understood that a number of techniques and steps are disclosed. Each of these has individual benefit and each can also be used in conjunction with one or more, or in some cases all, of the other disclosed techniques.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

As used herein, the term "substantially," when referring to a value, an activity, or to an amount of a composition, mass, weight, temperature, time, volume, concentration, percentage, etc., is meant to encompass variations of in some embodiments ±40%, in some embodiments ±30%, in some embodiments ±20%, in some embodiments ±10%, in some embodiments ±5%, in some embodiments 1%, in some embodiments ±0.5%, and in some embodiments ±0.1% from the specified amount, as such variations are appropriate to perform the disclosed methods or employ the disclosed compositions. For example, a composition is "substantially non-degradable" or "substantially non-resorbable" when it is at least 60%, or at least 75%, or at least 80%, or at least 85%, or at least 90%, or at least 95%, and, in certain cases, at least 99% non-degradable or non-resorbable.

Therapeutic Definitions

The terms "additional therapeutically active compound" or "additional therapeutic agent", as used in the context of the present disclosure, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated. Disease and disorders being treated by the additional therapeutically active agent include, for example, hypertension and diabetes. The additional compounds may also be used to treat symptoms associated with the injury, disease or disorder, including, but not limited to, pain and inflammation. Such compounds or agents include, but are not limited to drugs, antimicrobials, growth factors, cytokines, etc.

The term "adult" as used herein, is meant to refer to any non-embryonic or non-juvenile subject. For example, the term "adult adipose tissue stem cell," refers to an adipose stem cell, other than that obtained from an embryo or juvenile subject.

A disease, condition, or disorder is "alleviated" if the severity of a symptom of the disease, condition, or disorder, or the frequency with which such a symptom is experienced by a subject, or both, are reduced.

As used herein, an "analog" of a chemical compound is a compound that, by way of example, resembles another in structure but is not necessarily an isomer (e.g., 5-fluorouracil is an analog of thymine).

The term "antimicrobial agents" as used herein refers to any naturally-occurring, synthetic, or semi-synthetic compound or composition or mixture thereof, which is safe for human or animal use as practiced in the methods of this disclosure, and is effective in killing or substantially inhibiting the growth of microbes. "Antimicrobial" as used herein, includes antibacterial, antifungal, and antiviral agents.

"Antiviral agent," as used herein means a composition of matter which, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, Retrovir® Glaxo Wellcome Inc., Research Triangle Park, NC) is an antiviral agent which is thought to prevent replication of HIV in human cells.

The term "autologous", as used herein, refers to something that occurs naturally and normally in a certain type of tissue or in a specific structure of the body. In transplantation, it refers to a graft in which the donor and recipient areas are in the same individual, or to blood that the donor has previously donated and then receives back, usually during surgery.

The term "basal medium", as used herein, refers to a minimum essential type of medium, such as Dulbecco's Modified Eagle's Medium, Ham's F12, Eagle's Medium, RPMI, AR8, etc., to which other ingredients may be added. The term does not exclude media which have been prepared or are intended for specific uses, but which upon modification can be used for other cell types, etc.

The term "biocompatible," as used herein, refers to a material that does not elicit a substantial detrimental response in the host.

The term "biodegradable," as used herein, means capable of being biologically decomposed. A biodegradable material differs from a non-biodegradable material in that a biodegradable material can be biologically decomposed into units which may be either removed from the biological system and/or chemically incorporated into the biological system. Correspondingly, the term "non-degradable", as used herein, means incapable of being biologically decomposed, or at least highly resistant to biological decomposition or degradation.

The term "bioresorbable," as used herein, refers to the ability of a material to be resorbed in vivo. "Full" resorption means that no significant extracellular fragments remain. The resorption process involves elimination of the original implant materials through the action of body fluids, enzymes, or cells. Resorbed calcium carbonate may, for example, be redeposited as bone mineral, or by being otherwise re-utilized within the body, or excreted. "Strongly bioresorbable," as the term is used herein, means that at least 80% of the total mass of material implanted is resorbed within one year. Correspondingly, the term "non-resorbable", as used herein, means incapable of being bioresorbed, or at least highly resistant to bioresorption.

The term "clearance," as used herein refers to the physiological process of removing a compound or molecule, such as by diffusion, exfoliation, removal via the bloodstream, and excretion in urine, or via sweat or other fluid.

A "compound," as used herein, refers to any type of substance or agent that is commonly considered a drug, therapeutic, pharmaceutical, small molecule, or a candidate for use as the same, as well as combinations and mixtures of the above.

A "control" subject is a subject having the same characteristics as a test subject, such as a similar type of dependence, etc. The control subject may, for example, be examined at precisely or nearly the same time the test subject is being treated or examined. The control subject may also, for example, be examined at a time distant from the time at which the test subject is examined, and the results of the examination of the control subject may be recorded so that the recorded results may be compared with results obtained by examination of a test subject.

A "test" subject is a subject being treated or receiving a therapy.

"Cytokine," as used herein, refers to intercellular signaling molecules, the best known of which are involved in the regulation of mammalian somatic cells. A number of families of cytokines, both growth promoting and growth inhibitory in their effects, have been characterized including, for example, interleukins, interferons, and transforming growth factors. A number of other cytokines are known to those of skill in the art. The sources, characteristics, targets and effector activities of these cytokines have been described.

The term "decreased blood flow", as used herein, refers to a decrease in blood flow at a site of injury, disease, or disorder, and includes, but is not limited, a decrease in flow rate, an increase in stasis, and an increase in sludging in the vessels.

The term "delivery vehicle" refers to any kind of device, material, composition or mixture, which can be used to deliver an active agent, a drug, a therapeutic, cells, or the like, in vivo or can be added to a composition comprising the same to be administered to a subject or animal. This includes, but is not limited to, implantable devices, aggregates of cells, matrix materials, gels, etc.

As used herein, a "derivative" of a compound refers to a chemical compound that may be produced from another compound of similar structure in one or more steps, as in replacement of, for example, H by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, but are not limited to, radioactive isotopes, antigenic determinants, enzymes, nucleic acids available for hybridization, chromophores, fluorophores, chemiluminescent molecules, electrochemically detectable molecules, and molecules that provide for altered fluorescence polarization or altered light scattering.

A "disease" is a state of health of an animal or subject wherein the animal or subject cannot maintain homeostasis, and wherein if the disease is not ameliorated then the animal's/subject's health continues to deteriorate. As used herein, normal aging is included as a disease.

A "disorder" in an animal or subject is a state of health in which the animal or subject is able to maintain homeostasis, but in which the animal's/subject's state of health is less favorable than it would be in the absence of the disorder. Left untreated, a disorder does not necessarily cause a further decrease in the animal's/subject's state of health.

As used herein, an "effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, a "functional" molecule or compound is a molecule or compound in a form in which it exhibits a property or activity by which it is characterized. A functional enzyme, for example, is one that exhibits the characteristic catalytic activity by which the enzyme is characterized.

"Graft" refers to any free (unattached) cell, tissue, or organ for transplantation.

"Allograft" refers to a transplanted cell, tissue, or organ derived from a different animal of the same species.

"Xenograft" refers to a transplanted cell, tissue, or organ derived from an animal of a different species.

The term "growth factor" as used herein means a bioactive molecule that promotes the proliferation of a cell or tissue. Growth factors useful in the present disclosure include, but are not limited to, transforming growth factor-alpha (TGF-α), transforming growth factor-beta (TGF-β), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor, stem cell factor (SCF), keratinocyte growth factor (KGF), skeletal growth factor, bone matrix derived growth factors, and bone derived growth factors and mixtures thereof. Some growth factors may also promote differentiation of a cell or tissue. TGF, for example, may promote growth and/or differentiation of a cell or tissue.

The term "improved blood flow," as used herein, refers to increased blood flow in a subject being treated according to the methods of the disclosure compared with the flow in a subject with an otherwise identical injury or condition not being treated according to the methods of the disclosure. Improved blood flow is determined by methods such as those described herein and can include less stasis, less sludging, or a combination of both, in the subject being treated compared with the untreated subject.

The term "immunogenic", as used herein, is the ability of a particular substance or composition to provoke an immune response in the body of a human and other animal. In other words, immunogenicity is the ability to induce a humoral and/or cell-mediated immune responses. Correspondingly, the term "non-immunogenic", as used herein, means incapable of, or substantially incapable of, provoking an immune response in the body of a human and other animal.

The term "ingredient" refers to any compound, whether of chemical or biological origin, that can be used in cell culture media to maintain or promote the proliferation, survival, or differentiation of cells. The terms "component," "nutrient", "supplement", and ingredient" can be used interchangeably and are all meant to refer to such compounds. Typical non-limiting ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

As used herein "injecting" or "applying" includes administration of a compound of the disclosure by any number of routes and/or approaches including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal routes and/or approaches.

As used herein, "injury" generally refers to damage, harm, or hurt; usually applied to damage inflicted on the body by an external force.

As used herein, an "instructional material" includes a publication, a recording, a diagram, or any other medium of expression which can be used to communicate the usefulness of a compound of the disclosure in the kit for effecting alleviation of the various diseases or disorders recited herein. Optionally, or alternately, the instructional material may describe one or more methods of alleviating the diseases or disorders in a subject. The instructional material of the kit of the disclosure may, for example, be affixed to a container which contains the identified compound disclosure or be shipped together with a container which contains the identified compound. Alternatively, the instructional material may be shipped separately from the container with the intention that the instructional material and the compound be used cooperatively by the recipient.

Used interchangeably herein are the terms "isolate" and "select".

The term "isolated", when used in reference to cells, refers to a single cell of interest, or population of cells of interest, at least partially isolated from other cell types or other cellular material with which it naturally occurs in the tissue of origin (e.g., adipose tissue). A sample of stem cells is "substantially pure" when it is at least 60%, or at least 75%, or at least 90%, and, in certain cases, at least 99% free of cells other than cells of interest. Purity can be measured by any appropriate method, for example, by fluorescence-activated cell sorting (FACS), or other assays, which distinguish cell types.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to either a molecule that joins two other molecules covalently or non-covalently, e.g., through ionic or hydrogen bonds or van der Waals interactions.

The term "material", as used herein, refers to synthetic and natural materials such as matrix components. The term "materials and compounds" as used herein, refers to, inter alia, materials, compounds, cells, peptides, nucleic acids, drugs, matrix components, and imaging agents.

The term "modulate", as used herein, refers to changing the level of an activity, function, or process. The term "modulate" encompasses both inhibiting and stimulating an activity, function, or process. The term "modulate" is used interchangeably with the term "regulate" herein.

The term "musculoskeletal" as used herein encompasses the general broad meaning of the term, i.e., an organ system that gives a subject the ability to physically move, by using the muscles and skeletal system. Apart from locomotion, the skeleton also lends support and protects internal organs. Musculoskeletal diseases include, but are not limited to, diseases of the muscles and their associated ligaments, and other connective tissue and of the bones and cartilage viewed collectively. Musculoskeletal disorders include, for example, problems such as low back pain, joint injuries and repetitive strain injuries of various sorts.

The term "nanoparticle" or "particle" refers to a particle of any shape having the size of up to about 100 nanometers.

"Osteogenesis" as used herein refers to bone growth, bone remodeling, and repair of bone due to injury or disease.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration includes, but is not limited to, subcutaneous, intraperitoneal, intramuscular, intrasternal injection, and kidney dialytic infusion techniques.

"Permeation enhancement" and "permeation enhancers" as used herein relate to the process and added materials which bring about an increase in the permeability of skin to a poorly skin permeating pharmacologically active agent, i.e., so as to increase the rate at which the drug permeates through the skin and enters the bloodstream.

"Permeation enhancer" is used interchangeably with "penetration enhancer".

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The term "prevent," as used herein, means to stop something from happening, or taking advance measures against something possible or probable from happening. In the context of medicine, "prevention" generally refers to action taken to decrease the chance of getting a disease or condition.

A "prophylactic" treatment is a treatment administered to a subject who does not exhibit signs of a disease or injury or exhibits only early signs of the disease or injury for the purpose of decreasing the risk of developing pathology associated with the disease or injury.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

The term "regulate" refers to either stimulating or inhibiting a function or activity of interest.

A "reversibly implantable" device is one which may be inserted (e.g. surgically or by insertion into a natural orifice of the animal) into the body of an animal and thereafter removed without great harm to the health of the animal.

A "sample," as used herein, refers to a biological sample from a subject, including, but not limited to, normal tissue samples, diseased tissue samples, biopsies, blood, saliva, feces, semen, tears, and urine. A sample can also be any other source of material obtained from a subject which contains cells, tissues, or fluid of interest.

As used herein, "scaffold" refers to a supporting framework, such as one for bone or tissue growth, either in vivo or in vitro.

The term "skin," as used herein, refers to the commonly used definition of skin, e.g., the epidermis and dermis, and the cells, glands, mucosa, and connective tissue which comprise the skin.

The terms "solid support", "surface" and "substrate" are used interchangeably and refer to a structural unit of any size, where said structural unit or substrate has a surface suitable for immobilization of molecular structure or modification of said structure and said substrate is made of a material such as, but not limited to, metal, metal films, glass, fused silica, synthetic polymers, and membranes.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. "Standard" can also refer to an "internal standard", such as an agent or compound which is added at known amounts to a sample and which is useful in determining such things as purification or recovery rates when a sample is processed or subjected to purification or extraction procedures before a marker of interest is measured. Internal standards are often but are not limited to, a purified marker of interest which has been labeled, such as with a radioactive isotope, allowing it to be distinguished from an endogenous substance in a sample.

The term "stimulate" as used herein, means to induce or increase an activity or function level such that it is higher relative to a control value. The stimulation can be via direct or indirect mechanisms. In one aspect, the activity or function is stimulated by at least 10% compared to a control value, more preferably by at least 25%, and even more preferably by at least 50%. The term "stimulator" as used herein, refers to any composition, compound or agent, the application of which results in the stimulation of a process or function of interest, including, but not limited to, wound healing, angiogenesis, bone healing, osteoblast production and function, and osteoclast production, differentiation, and activity.

A "subject" of diagnosis or treatment can in some embodiments be a mammal, including a human. In some aspects, the terms "subject", "patient" or "recipient" as used herein, can be used interchangeably and can refer to a member of any invertebrate or vertebrate species. Accordingly, the term "subject" is intended to encompass any member of the Kingdom Animalia including, but not limited to the phylum Chordata (e.g., members of Classes Osteichythyes (bony fish), Amphibia (amphibians), Reptilia (reptiles), Aves (birds), and Mammalia (mammals)), and all Orders and Families encompassed therein.

As used herein, a "subject in need thereof" is a patient, animal, mammal, or human, who will benefit from the method of this disclosure.

A "surface active agent" or "surfactant" is a substance that has the ability to reduce the surface tension of materials and enable penetration into and through materials.

The term "symptom," as used herein, refers to any morbid phenomenon or departure from the normal in structure, function, or sensation, experienced by the patient and indicative of disease. In contrast, a sign is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "thermal injury" is used interchangeably with "thermal burn" herein.

A "thermal-sensitive" gel system undergoes a phase transition when induced by temperature.

"Tissue" means (1) a group of similar cells united to perform a specific function; (2) a part of an organism consisting of an aggregate of cells having a similar structure and function; and/or (3) a grouping of cells that are similarly characterized by their structure and function, such as muscle or nerve tissue.

The term "tissue injury-associated decreased blood flow", as used herein, refers to the decrease in blood flow which occurs following an injury, such as a thermal injury, to a tissue. The decrease in blood flow includes, but is not limited to, decreased volume, rate, stasis, or sludging. One of ordinary skill in the art will appreciate that there are multiple parameters which can be used as measures or signs of decreased blood flow, as well as multiple techniques to determine decreased blood flow.

The term "topical application," as used herein, refers to administration to a surface, such as the skin. This term is used interchangeably with "cutaneous application" in the case of skin. A "topical application" is a "direct application".

By "transdermal" delivery is meant delivery by passage of a drug through the skin or mucosal tissue and into the bloodstream. Transdermal also refers to the skin as a portal for the administration of drugs or compounds by topical application of the drug or compound thereto. "Transdermal" is used interchangeably with "percutaneous."

As used herein, the term "treating" may include prophylaxis of the specific injury, disease, disorder, or condition, or alleviation of the symptoms associated with a specific injury, disease, disorder, or condition and/or preventing or eliminating said symptoms if specifically stated as being a prophylactic treatment. A "prophylactic" treatment is a treatment administered to a subject who does not exhibit signs of a disease or exhibits only early signs of the disease for the purpose of decreasing the risk of developing pathology associated with the disease. "Treating" is used interchangeably with "treatment" herein.

As used herein "wound" or "wounds" may refer to any detectable break in the tissues of the body, such as injury to skin or to an injury or damage, or to a damaged site associated with a disease or disorder. Although the terms "wound" and "injury" are not always defined exactly the same way, the use of one term herein, such as "injury", is not meant to exclude the meaning of the other term.

Chemical Definitions

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically, $C_1$-$C_6$ alkyl groups include, but are not limited to, methyl, ethyl, n-propyl, iso-propyl, butyl, iso-butyl, sec-butyl, tert-butyl, pentyl, hexyl, and the like.

The term "$C_2$-$C_n$ alkenyl" wherein n is an integer, as used herein, represents an olefinically unsaturated branched or linear group having from two to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2$-$C_n$ alkynyl" wherein n is an integer refers to an unsaturated branched or linear group having from two to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3$-$C_n$ cycloalkyl" wherein n=8, represents cyclopropyl, cyclobutyl, cyclopentyl, cyclohexyl, cycloheptyl, and cyclooctyl.

As used herein the term "aryl" refers to an optionally substituted mono- or bicyclic carbocyclic ring system having one or two aromatic rings including, but not limited to, phenyl, benzyl, naphthyl, tetrahydronaphthyl, indanyl, indenyl, and the like. Optionally substituted aryl includes aryl compounds having from zero to four substituents, and Asubstituted aryl@ includes aryl compounds having one or more substituents. The term ($C_5$-$C_8$ alkyl)aryl refers to any aryl group which is attached to the parent moiety via the alkyl group.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "heterocyclic group" refers to an optionally substituted mono- or bicyclic carbocyclic ring system containing from one to three heteroatoms wherein the heteroatoms are selected from the group consisting of oxygen, sulfur, and nitrogen.

As used herein the term "heteroaryl" refers to an optionally substituted mono- or bicyclic carbocyclic ring system having one or two aromatic rings containing from one to three heteroatoms and includes, but is not limited to, furyl, thienyl, pyridyl and the like.

A "meroxapol" is polyoxypropylene-polyoxyethylene block copolymer with the general formula $HO(C_3H_6O)_a(C_2H_4O)_b(C_3H_6O)_aH$. It is available in different grades. Each meroxapol name is followed by a code number according to the average numerical values of the respective monomers units denoted by "a" and "b".

As used herein, the term "optionally substituted" refers to from zero to four substituents, wherein the substituents are each independently selected. Each of the independently selected substituents may be the same or different than other substituents.

A "poloxamer" is a nonionic polyoxyethylene-polyoxypropylene block co-polymer with the general formula $HO(C_2H_4O)_a(C_3H_6O)_b(C_2H_4O)_aH$. It is available in different grades, which vary from liquids to solids. Each poloxamer name is followed by a code number according to the average numerical values of the respective monomers units denoted by "a" and "b".

A "poloxamine" is a polyoxyethylene-polyoxypropylene block copolymer of ethylene diamine with the general formula $[HO(C_2H_4O)(C_3H_6O)_bC_3H_6]_2NCH_2CH_2N—[C_3H_6(OC_3H_6)_b(OC_2H_4)_aOH]_2$. It is available in different grades. Each poloxamine name is followed by a code number according to the average numerical values of the respective monomers units denoted by "a" and "b".

The compounds of the present disclosure contain one or more asymmetric centers in the molecule. In accordance with the present disclosure a structure that does not designate the stereochemistry is to be understood as embracing all the various optical isomers, as well as racemic mixtures thereof.

The compounds of the present disclosure may exist in tautomeric forms and the disclosure includes both mixtures and separate individual tautomers. For example, the following structure:

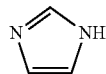

is understood to represent a mixture of the structures:

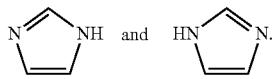

The terminology used herein is for the purpose of describing the particular versions or embodiments only, and is not intended to limit the scope of the present disclosure. All publications mentioned herein are incorporated by reference in their entirety.

Hydrogel Compositions and Methods of Using

As discussed further below, provided herein are non-degradable, non-immunogenic microporous hydrogel compositions. Such compositions can in some aspects comprise a collection of flowable hydrogel particles comprising a bioinert polymeric backbone (e.g., poly(ethylene glycol) (PEG)-based polymeric backbone), an annealing component comprising a physiologically-stable, radically polymerizable alkene (e.g., methacrylamide), wherein the annealing component links the flowable hydrogel particles, and a heparin compound. See, FIG. 1B. Advantageously, such compositions are substantially non-degradable (non-resorbable) and substantially non-immunogenic. In some aspects, such non-immunogenic microporous hydrogel compositions include heparin that is heterogeneously distributed throughout the microporous hydrogel composition. The unevenly distributed heparin can in some aspects form heparin islands within the microporous hydrogel composition. In some aspects, such heparin islands comprise single or clustered groups of microgels or hydrogels, isolated within the microporous hydrogel composition. In some aspects, MAP hydrogel compositions disclosed herein comprise a synthesized 4-armed PEG, wherein approximately 1 to 2 arms of the 4-armed PEG comprise a maleimide functional group, and wherein approximately 2 to 3 arms of the 4-armed PEG comprise a methacrylamide functional group.

Also disclosed herein are methods of treating a tissue, including delivering to the tissue a non-degradable, non-immunogenic microporous hydrogel composition in accordance with the presently disclosed subject matter, and exposing the non-degradable, non-immunogenic microporous hydrogel composition to an annealing initiator to thereby anneal the flowable hydrogel particles to form a stabilized scaffold, such as a covalently-stabilized scaffold, of hydrogel particles. As discussed further herein, the tissue to be treated comprises a laryngeal vocal fold, more specifically the superficial lamina propria and/or vocalis muscle, and in some aspects, the treatment can be in a subject suffering from glottic incompetence and/or a subject in need of laryngeal reconstruction.

In some aspects, the annealing component can comprise any physiologically-stable, radically polymerizable alkene wherein the annealing component links the flowable hydrogel particles. Any alkene that remains approximately 90% unaltered after about 24 hours in situ would be considered a physiologically-stable, radically polymerizable alkene. An example of such a physiologically-stable, radically polymerizable alkene is methacrylamide.

In some embodiments, hydrogel compositions can be modified to retain or increase their useful characteristics as disclosed herein. In one embodiment, components can be modified to obtain the desired characteristics.

The present disclosure further provides compositions and methods for treating an injury, disease, or disorder in a subject. In one embodiment, the method comprises administering to a subject a pharmaceutical composition comprising a non-degradable, non-immunogenic microporous hydrogel composition of the disclosure and an effective amount of at least one cell, material, or compound useful for treating the injury, disease, or disorder. In some embodiments, the non-degradable, non-immunogenic microporous hydrogel composition can comprise a thermo-gelling solution.

In one aspect, the injury, disease, or disorder can comprise a musculoskeletal-associated injury, disease, or disorder.

In one aspect, the material or compound can be selected from the group comprising drugs, antimicrobial agents, peptides, growth factors, cytokines, nucleic acids, matrix components, and imaging agents.

In one aspect, a cell type useful for treatment, includes, but is not limited to, a cell selected from the group consisting of stem cells, pluripotent stem cells, committed stem cells, embryonic stem cells, adult stem cells, bone marrow stem cells, bone marrow-derived stem cells, adipose stem cells, mesenchymal stem cells, umbilical cord stem cells, dura mater stem cells, precursor cells, differentiated cells, osteoblasts, osteoclasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons. In some embodiments, the cell is a human cell.

The instant disclosure further provides compositions and methods for delivering a cell, material or compound to a subject in need thereof, comprising administering to the subject a MAP hydrogel of the present disclosure, wherein the MAP hydrogel composition can further comprise a cell, material, or compound. In some embodiments the composition can further comprise a pharmaceutical compound.

Thus, in some embodiments, provided herein are non-degradable, non-immunogenic microporous hydrogel compositions that comprise a collection of flowable hydrogel particles comprising a bioinert polymeric backbone, an annealing component comprising a physiologically-stable, radically polymerizable alkene, wherein the annealing component links the flowable hydrogel particles, and a heparin compound. The microporous hydrogel composition can be substantially non-degradable and substantially non-immunogenic. In some aspects, the bioinert polymeric backbone can comprises a poly(ethylene glycol)(PEG), and the physiologically-stable, radically polymerizable alkene can comprise a methacrylamide.

In some aspects, the heparin compound can comprise a thiolated heparin, wherein the concentration can be about 1 mg/ML to about 200 mg/mL, preferably about 1 mg/mL to about 20 mg/mL, and more preferably about 1 mg/mL to about 5 mg/mL. The heparin compound can be heterogeneously distributed throughout the microporous hydrogel composition. In some embodiments, the heparin compound can be unevenly distributed throughout the microporous hydrogel composition to thereby form heparin islands, comprising single or clustered groups of microgels, isolated within the microporous hydrogel composition. The concentration of the heparin compound can range from about 1 mg/mL to about 20 mg/mL. Moreover, in some aspects, such compositions can comprise heterogenous mixtures of hydrogel particles with a heparin compound and hydrogel particles without a heparin compound, wherein the ratio of hydrogel particles with a heparin compound to hydrogel particles without a heparin compound is about 1:100, preferably optionally about 1:25, or more preferably about 1:10. The heparin compound can comprise a heparin having a molecular weight of about kDa to about 25 kDa. The heparin can comprise a low molecular weight (LMW) to high molecular weight (HMW) heparin comprising variable molecular weights (MW 0.5 kDa to 50 kDa), including intentional mixtures thereof.

In some aspects, such non-immunogenic microporous hydrogel composition can comprise a synthesized 4-armed PEG, optionally wherein approximately 1 to 2 arms of the 4-armed PEG comprise a maleimide functional group, and wherein approximately 2 to 3 arms of the 4-armed PEG comprise a methacrylamide functional group.

In some embodiments, the concentration of methacrylamide can be about 0.5 mM to about 1 mM. Annealing can occur in about 10% of the time of a hydrogel without the methacrylamide.

Such compositions can further comprise an annealing initiator, wherein activation of the annealing initiator can cause annealing of the flowable hydrogel particles to form a scaffold of hydrogel particles having interstitial spaces therein. The annealing initiator is activated by long wave ultra-violet (UV), visible, or infrared light. Additionally, in some aspects, the annealing initiator can comprise a photoinitiator or a thermal initiator.

In some embodiments, at least a portion of the flowable hydrogel particles can further comprise a PEG crosslinker. The amount of PEG in the composition ranges from about 0.5 wt % to about 10 wt %. The amount of PEG in the composition can be selected to match a biomechanical property of a tissue.

In some aspects, the backbone polymer comprises a poly(ethylene glycol), hyaluronic acid, polyacrylamide, and/or polymethacrylate. The substantially non-degradable microporous hydrogel can be configured to resist degradation in vivo for at least 90 days, preferably at least 180 days, most preferably indefinitely. Furthermore, such compositions can be configures such that less than about 40% of cells present within the microporous hydrogel composition following 6 months in vivo are immune cells.

Treatment of Glotic Incompetence and Other Conditions

The role of the larynx in voice production is to convert aerodynamic energy from the chest and lungs into acoustic energy. Critical in this process is vocal fold adduction, which potentiates glottal valve closure. Glottic incompetence is a common laryngeal disorder that can cause dysphonia (loss of speech) and dysphagia (dysfunctional swallowing), which significantly diminishes an individual's quality of life. Causes of glottic incompetence include vocal fold atrophy, unilateral vocal fold paresis and paralysis, vocal fold scarring, and tissue loss due to surgery or radiation therapy.

Laryngeal reconstruction is the gold standard of care for moderate to severe glottic incompetence; however, this procedure is invasive and exposes patients to surgical complications. Several permanent materials such as Gore-Tex®, silastic, and titanium are used for laryngeal reconstruction; however, these materials require surgical implantation and fail to reproduce the physical properties and geometry of the surrounding tissue and can result in chronic inflammation, infection, implant migration, and extrusion. An alternative treatment to reconstructive surgery is medialization of the impaired vocal fold with injectable fillers. Medialization involves augmenting the size of the affected vocal fold, providing a medialized surface for the unaffected vocal fold to perform dynamic glottic functions of respiration, deglutition, and phonation (FIG. 1A, left pane pre-medialization, right panel post-medialization). Injectable biomaterials (e.g. hyaluronic acid, collagen, etc.) have several advantages, including the ability to be quickly and non-invasively administered in an outpatient setting. Unfortunately, these materials are typically naturally derived and thus short-lived (due to the presence of degradative enzymes), typically lasting from several days to months. One of the most successful injectables is crosslinked hyaluronic acid, however this material begins to fail approximately 3-6 months after treatment. Synthetic injectable biomaterials have the potential for longer effects, but until recently, lacked good integration with host tissue without providing for duration-limiting degradative behavior (e.g. hydrolysis).

To address this need, disclosed herein in some embodiments is a synthetic, injectable, and easy-to-apply product that permanently restores vocal fold function and quickly affixes through integration with the surrounding tissue.

MAP hydrogels are materials comprising microscale spherical building blocks with completely tunable physical and degradation properties. MAP gel shows excellent tissue integration that is independent of degradation due to interconnected microporosity. However, MAP was originally produced as a wound-healing scaffold with the intent of being resorbed by the body following healing. Therefore, as disclosed herein, several MAP parameters required modification and engineering to meet the demands of permanently treating glottis incompetence and other conditions requiring dermal and subdermal filling.

In some embodiments, MAP hydrogel was optimized to meet the physical parameters needed for effective treatment, including being non-resorbable and matching the physical characteristics of ex vivo vocal tissue (in some aspects using porcine vocal tissue as a model). MAP tissue integration was designed using chemotaxis for influencing cellular migration. The disclosed MAP hydrogel compositions disclosed herein were validated as effective in vivo therapeutics, including for example for treating glottic incompetence, using a leporine (rabbit) model (see Examples below).

Provided in accordance with some embodiments of the presently disclosed subject matter is a non-degradable chemistry which can be formed into microparticles. In some embodiments a combination of 4 arm PEG macromers (bioinert) are employed in the formation of the microparticles. Unlike most hydrogels, these microparticles allow for a porous environment, which promotes cellular infiltration and tissue remodeling. In some embodiments, using a radical polymerization approach the presently disclosed particles can be annealed with white light to be locked into place and achieve desired properties. Thus, provided in accordance with some embodiments of the presently disclosed subject matter are Microporous Annealed Particles (MAPs), which are employed in hydrogels. MAP hydrogels provide for increased cellular infiltration and quickened tissue remodeling. In some embodiments, the MAP hydrogels can be produced by radical polymerization with five (5) minutes or less exposure to white light. In some embodiments, PEG macromers modified with tunable mechanical and degradation properties are employed in MAP hydrogels in accordance with the presently disclosed subject matter.

In some embodiments, the presently disclosed subject matter provides a microporous hydrogel scaffold for biomedical applications comprising a plurality of MAPs that are annealed to one another in an annealing reaction. The annealing reaction, in one aspect of the subject matter described herein, forms covalent bonds between adjacent particles. For example, in the post-annealed state, the scaffold forms a three-dimensional structure that conforms to the site of application or delivery. Because of the imperfect packing of the particles, the annealed scaffold formed from the particles includes interstitial spaces formed therein where cells can migrate, bind, and grow. The formed scaffold structure is porous upon annealing. This porosity includes the interstitial spaces mentioned above as well as nanoscopic pores that may be created or formed in the particles themselves. The micro-porosity of the scaffold structure allows for high diffusivity of nutrients, cell growth and differentiation factors, as well as cell migration, ingrowth, and penetration.

Additionally, the microporosity of the scaffold provides for cellular infiltration and tissue remodeling, while maintaining overall scaffold integrity. In addition, by not limiting the biomaterial to natural materials, the degradation profile and physical properties (e.g., stiffness, internal diffusivity, etc.) are improved, for example, by having a larger available range and a wider array of biological signals or therapeutically-active chemicals can be included within the material (e.g., antibiotics, steroids, growth factors, and the like can be loaded into the scaffold). Furthermore, the release or elution of the drugs, compounds, or other material to trigger or control biological activity, in certain embodiments, can be tuned through modification of the desired biomaterial. The signal compounds or molecules may also be released or eluted into the affected area after initial placement of the scaffold at the delivery site.

The pre-delivery formation of the MAPs allows for controlled mechanical tunability of the resultant formed scaffold to match the properties of the surrounding tissue, i.e. biomechanical matching. For example, vocal folds stiffness can range from about 2 kPa to about 40 kPa. As such, a composition for treating glottic incompetence can be tuned to yield a similar stiffness. As another example, when replacing lipoatrophy in the face a composition can be tuned to match younger facial elasticity to provide for a biomechanically tuned volumetric face lift. Moreover, the microporous nature of the annealed scaffold is beneficial to reduce immune foreign body response to the scaffold.

Figure 2:
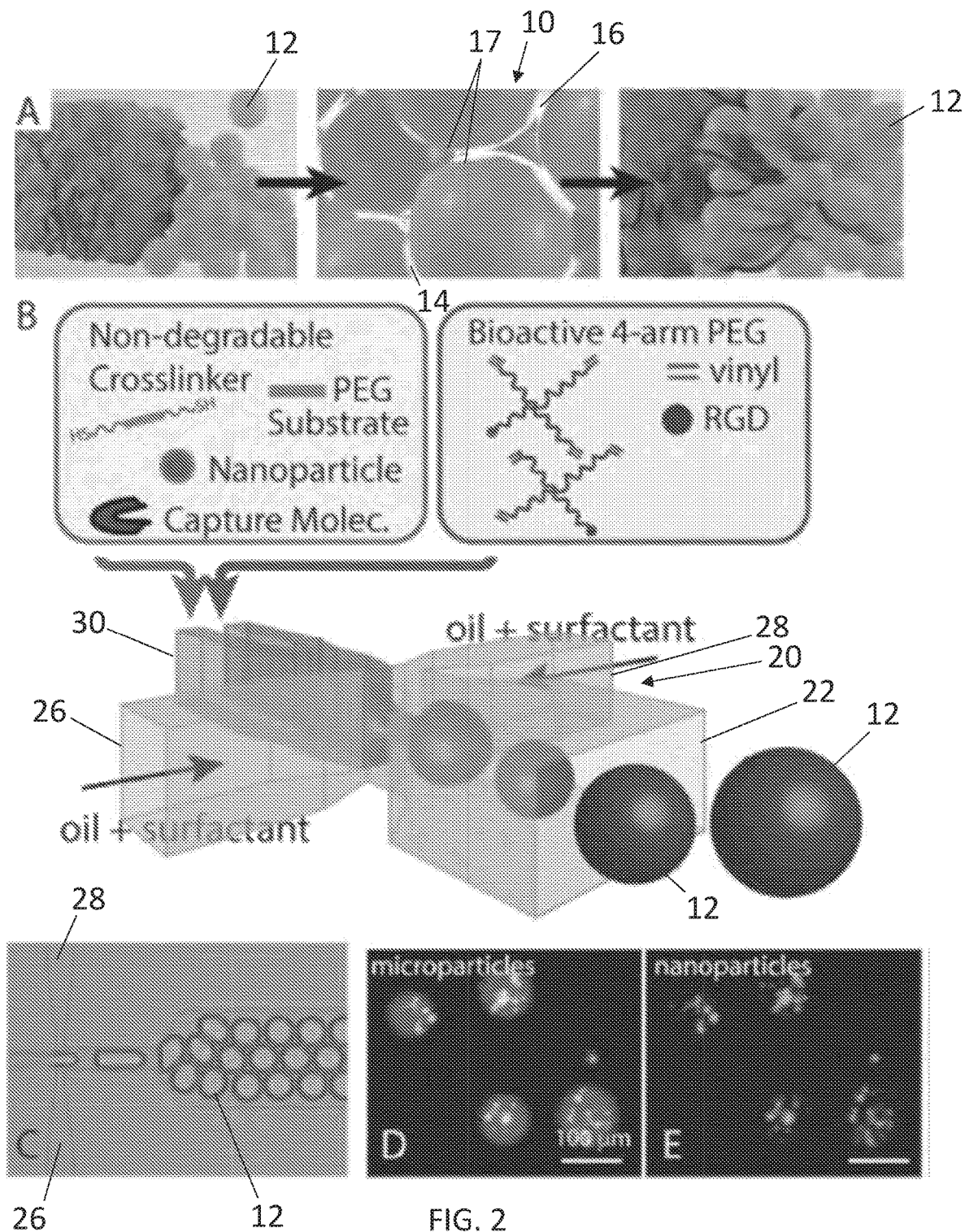

Referring now to FIGS. 2A-2C, in some embodiments, a portion of the formed three-dimensional scaffold 10 is formed by a plurality of annealed hydrogel particles 12. The scaffold 10 includes interstitial spaces therein 14 that are voids that form micropores within the larger scaffold 10. The interstitial spaces 14 have dimensions and geometrical profiles that permit the infiltration, binding, and growth of cells. It should be appreciated that the microporous nature of the scaffold 10 disclosed herein involves a network of interstitial spaces or voids 14 located between annealed MAPs 12 that form the larger scaffold structure. In one embodiment, the interstitial spaces or voids 14 created within the scaffold 10 exhibit negative concavity (e.g., the interior void surface is convex). FIGS. 2A-2C illustrate an exemplary void 14 with void walls 16 exhibiting negative concavity. The negative concavity is caused because the particles 12 that are annealed to one another are generally or substantially spherical in shape in one embodiment. This allows for the packing of particles 12 that, according to one embodiment, produces a low void volume fraction between about 10% and about 50% and, in another embodiment between about 26% to about 36%. While the void volume fraction is low, the negative concavity exhibited in certain embodiments within the network of voids 14 provides a relatively high surface area to void volume for cells to interact with. For a given volume of cells, they would then, on average, be exposed to even more and larger surfaces (e.g., on the void walls 16) to interact within the network of voids in the scaffold 10.

In some embodiments, the void network comprises regions where hydrogel surfaces are in close proximity (e.g., near neighboring annealed particles 12) leading to high surface area adhesive regions for cells to adhere and rapidly migrate through, while neighboring regions further in the gaps between particles 12 have a larger void space that can enable cell and tissue growth in this space. Therefore the combined adjacency of the tight void areas and more spacious void gaps is expected to have a beneficial effect on tissue ingrowth and regrowth, compared to either entirely small voids or all larger voids.

Note that in the embodiment described above, the negative concavity results due to the spherical shape of the particles 12. In other embodiments, the particles 12 might not be spherical in shape. Other nonspherical shapes may still be used in the scaffold 10. Still referring to FIG. 2A-2C, the scaffold is formed by particles 12 that are secured to one another via annealing surfaces 17. As explained herein, the annealing surfaces 17 are formed either during or after application of the particles 12 to the intended delivery site.

The scaffold 10 may be used for various applications, including a variety of medical applications such as treating glottic incompetence, vocal fold scar, and/or as dermal fillers. In the case of tissue filler applications for volume loss related to aging, lipoatrophy, lipodystrophy, dermal scarring, or superficial or deep rhytides, injection of the particles 12 directly into the dermis and subcutaneous adipose tissue via needle or cannula may be used to improve tissue contour, tissue loss, or tissue displacement. Because cells used in regenerative medicine can grow within the particles 12, cells (e.g., mesenchymal stem cells, fibroblasts, etc.) may be included as a therapy by initially polymerizing the cells (1-20 cells) within particles, or cells may be initially adhered to particles, or cells may be introduced with the particle solution (non-adhered), prior to annealing in situ in tissue.

The scaffold 10 may also be used for in vitro tissue growth, three-dimensional (3D) matrices for biological science studies, and cosmetic and dermatologic applications.

Micro fluidic formation enables substantially monodisperse hydrogel particles 12 to form into an interconnected microporous annealed particle scaffold 10 (in one aspect of the subject matter described herein), thereby enabling the controlled chemical, physical, and geometric properties of the hydrogel particles 12 (e.g., building blocks), to provide downstream control of the physical and chemical properties of the assembled scaffold 10. In vitro, cells incorporated during scaffold 10 formation proliferate and form extensive three-dimensional networks within forty-eight (48) hours. In vivo, the injectable gel system that forms the scaffold 10 facilitates cell migration.

Every treatment site varies in its physical, chemical, and other requirements for treatment, requiring a material strategy that is robust to a variety of challenging environments. The microporous gel system and the resulting scaffold 10 provides a stably linked interconnected network of micropores for cell migration and bulk integration with surrounding tissue. The microporous gel system achieves these favorable features by, according to some embodiments, using the self-assembly of hydrogel particles 12 as "building blocks" or "sub-units" formed by microfluidic water-in-oil droplet segmentation. According to one embodiment, the hydrogel particles 12 formed in this manner are substantially monodisperse. The hydrogel particles 12 can be injected and molded into any desired shape. Lattices of hydrogel particles 12 are then annealed to one another via surface functionalities to form an interconnected microporous scaffold 10 either with or without cells present in the interconnected porous networks. The scaffold 10, in some embodiments, includes covalently linked hydrogel particles 12 that form a three-dimensional scaffold 10.

By combining injectability and microporosity, the microporous gel system provides an ideal biomaterial scaffold for efficient cellular network formation in vitro and bulk tissue integration in vivo. Through microfluidic fabrication, the chemical, physical, and geometric properties of the hydrogel particles 12 can be predictably and uniformly tailored, allowing for downstream control of the properties of the emergent scaffolds 10. The novel building block-based approach in which robustly achieved imperfect self-assembly is desirable to achieve microporosity fundamentally changes the use and implementation of hydro gels as tissue mimetic constructs, providing a philosophical change in the approach to injectable scaffolding.

In some embodiments of the subject matter described herein, the microporous gel system uses hydrogel particles 12 having diameter dimensions within the range from about 5 µm to about 1,000 µm. Thus, hydrogel particles comprise microscale spherical building blocks, which are alternatively referred to herein in some case as microgel particles. The particles 12 may be made from a bioinert polymer, hydrophilic polymer, amphiphilic polymer, synthetic or natural polymer (e.g., poly(ethylene glycol) (PEG), poly(propylene glycol), poly(hydroxyethylmethacrylate), hyaluronic acid (HA), gelatin, fibrin, chitosan, heparin, heparan, and synthetic versions of HA, gelatin, fibrin, chitosan, heparin, or heparan). In one embodiment, the particle 12 is made from any natural (e.g., modified HA) or synthetic polymer (e.g., PEG) capable of forming a hydrogel. In one or more embodiments, a polymeric network and/or any other support network capable of forming a solid hydrogel construct may be used. Suitable support materials for most tissue engineering/regenerative medicine applications are generally biocompatible. Examples of suitable biocompatible supports include: natural polymeric carbohydrates and their synthetically modified, crosslinked, or substituted derivatives, such as gelatin, agar, agarose, crosslinked alginic acid, chitin, substituted and cross-linked guar gums, cellulose esters, especially with nitrous acids and carboxylic acids, mixed cellulose esters, and cellulose ethers; natural polymers containing nitrogen, such as proteins and derivatives, including cross-linked or modified gelatins, and keratins; vinyl polymers such as poly(ethyleneglycol)acrylate/methacrylate/vinyl sulfone/maleimide/norbornene/allyl, polyacrylamides, polymethacrylates, copolymers and terpolymers of the above polycondensates, such as polyesters, polyamides, and other polymers, such as polyurethanes; and mixtures or copolymers of the above classes, such as graft copolymers obtained by initializing polymerization of synthetic polymers on a preexisting natural polymer. A variety of biocompatible polymers are available for use in therapeutic applications; examples include: polycaprolactone, polyglycolide, polylactide, poly(lactic-co-glycolic acid) (PLGA), and poly-3-hydroxybutyrate. Methods for making networks from such materials are well-known.

In one or more embodiments, the hydrogel particles further include covalently attached chemicals or molecules that act as signaling modifications that are formed during particle 12 formation. Signaling modifications includes the addition of, for example, adhesive peptides, extracellular matrix (ECM) proteins, and the like. Functional groups and/or linkers can also be added to the particles 12 following their formation through either covalent methods or non-covalent interactions (e.g., electrostatic charge-charge interactions or diffusion limited sequestration). Crosslinkers are typically selected depending on the desired characteristic.

In one embodiment, the chemistry used to generate particles 12 allows for subsequent annealing and scaffold 10 formation through radically-initiated polymerization. This includes chemical-initiators such as ammonium persulfate combined with Tetramethylethylenediamine. Alternatively, photoinitiators such as Irgacure® 2959 or Eosin Y together with a free radical transfer agent such as a free thiol group (used at a concentration within the range of 10 µM and 1 mM) may be used in combination with a light source that is used to initiate the reaction as described herein. One example of a free thiol group may include, for example, the amino acid cysteine, as described herein. Of course, peptides including a free cysteine or small molecules including a free thiol may also be used. Another example of a free radical transfer agent includes N-Vinylpyrrolidone (NVP).

Alternatively, Michael and pseudo-Michael addition reactions, including α, β-unsaturated carbonyl groups (e.g., acrylates, vinyl sulfones, maleimides, and the like) to a nucleophilic group (e.g., thiol, amine, aminoxy) may be used to anneal particles 12 to form the scaffold 10. In another alternative embodiment, particle 12 formation chemistry allows for network formation through initiated sol-gel transitions including fibrinogen to fibrin (via addition of the catalytic enzyme thrombin).

Functionalities that allow for particle-particle annealing are included either during or after the formation of the particles 12. In one or more embodiments, these functionalities include α, β-unsaturated carbonyl groups that can be activated for annealing through either radical initiated reaction with α, β-unsaturated carbonyl groups on adjacent particles or Michael and pseudo-Michael addition reactions with nucleophilic functionalities that are either presented exogenously as a multifunctional linker between particles or as functional groups present on adjacent particles. This method can use multiple microgel particle 12 population types that when mixed form a scaffold 10. For example, microgel particle 12 of type X presenting, for example, nucleophilic surface groups can be used with microgel particle 12 type Y presenting, for example, α, β-unsaturated carbonyl groups. In another embodiment, functionalities that participate in Click chemistry can be included allowing for attachment either directly to adjacent microgel particles 12 that present complimentary Click functionalities or via an exogenously presented multifunctional molecule that participates or initiates (e.g., copper) Click reactions.

The annealing functionality can include any previously discussed functionality used for hydrogel crosslinking that is either orthogonal or similar (if potential reactive groups remain) in terms of its initiation conditions (e.g., temperature, light, pH) compared to the initial crosslinking reaction. For example, if the initial crosslinking reaction comprises a Michael-addition reaction that is temperature dependent, the subsequent annealing functionality can be initiated through temperature or photoinitiation (e.g., Eosin Y, IRGACURE®). As another example, the initial hydrogels may be photopolymerized at one wavelength of light or LASER (e.g., ultraviolet with Irgacure®), and annealing of the hydrogel particles 12 occurs at the same or another wavelength of light (e.g., visible with Eosin Y) or vice versa. In some embodiments, the initiator can be any initiator activated by long wave ultra-violet (UV), visible, or infrared light. By way of example and not limitation, Lithium phenyl-2,4,6-trimethylbenzoylphosphinate (LAP) is UV-activated. Still yet, in some embodiments heat can be used as an initiator of annealing, including for example the body temperature (e.g. 38.6 degrees Celsius) of the subject receiving the composition. Besides annealing with covalent coupling reactions, annealing moieties can include non-covalent hydrophobic, guest/host interactions (e.g., cyclodextrin), hybridization between complementary nucleic acid sequences or nucleic acid mimics (e.g., protein nucleic acid) on adjoining hydrogel particles 12, or ionic interactions. An example of an ionic interaction comprises alginate functionality on the hydrogel particle surfaces that are annealed with $Ca^{2+}$. So-called "A+B" reactions can be used to anneal hydrogel particles 12 as well. In this embodiment, two separate hydrogel types (type A and type B) are mixed in various ratios (between 0.01:1 and 1:100A:B) and the surface functionalities of type A react with type B (and vice versa) to initiate annealing. These reaction types may fall under any of the mechanisms listed herein.

In some embodiments, the hydrogel particles 12 are fabricated using either microfluidic or millifluidic methods, generating deterministic hydrogel particles length scales with small variability and in high throughput (e. g., frequencies greater than 10 particles/second). The coefficient of variation of the hydrogel particles 12 length scale (e.g., diameter) can be within 35% or more preferably within 15% and even more preferably within 5% of the mean length scale. Milli- or microfluidics allow for uniform, pre-determined, concise material properties to be included pre-, in-, and post-formation of hydrogel particles 12. Furthermore, the microfluidic/millifluidic production mechanism allows for ease of scaling up production as well as good quality control over chemical composition and physical characteristics of the hydrogel particles 12. The millifluidic and/or microfluidic technologies for hydrogel particle 12 generation are easily scalable processes to create large amounts of material for commercial needs, while maintaining high accuracy and precision in hydrogel particle 12 characteristics. Moreover, this is all accomplished at low cost in comparison to other technologies involving electrospinning or large-scale fibrin purification.

In one embodiment, hydrogel particles 12 are formed using automated fluidic methods relying on water-in-oil emulsion generation. This includes microfluidic or millifluidic methods utilizing glass/PDMS, PDMS/PDMS, glass/glass, or molded/cast/embossed plastic chips to create water in oil droplets with a size distribution variation that is less than 35%. Representative microfluidic or millifluidic methods are disclosed in Griffin et al., U.S. patent application Ser. No. 15/179,151, published on Sep. 29, 2016 as U.S. Patent Application Publication No. 2016/0279283, herein incorporated by reference in its entirety.

FIGS. 2A-2C illustrates one embodiment of a microfluidic that is used to generate the micro gel particles 12. The microfluidic device 20 is formed in a substrate material 22 such as PDMS which may include another substrate material (e.g., glass) that is bonded the substrate 22. In this embodiment, the micro fluidic device 20 includes a first inlet 26, a second inlet 28, and a third inlet 30. As seen in FIG. 2A, the third inlet 30 is interposed between the first inlet 26 and the second inlet 28. In this embodiment, the third inlet 30 is coupled to a solution containing a 4-arm poly(ethylene glycol) vinyl that has been pre-modified with oligopeptides for cell adhesive properties (e.g., RGD) and/or bioactive compounds for controlled protein interaction (e.g. heparin).

The fluidic conditions that lead to hydrogel particle 12 formation include, in some embodiments, on-chip mixing of a bioinert polymer-based or PEG-based and crosslinker-based aqueous solutions, where one part contains base polymer and the other contains the crosslinking or initiating agent. Of course, in the embodiment of FIGS. 2A-2C, there is a three-input mixing which includes the aforementioned components plus the addition of the aqueous-based inert stream. These PEG and crosslinker solutions are mixed at either a 1:1 volumetric ratio, or another controllable ratio (controlled by relative flow rates into the device) up to 1:100. The ratios of the oil and total aqueous flow rates are controlled to determine a specific size hydrogel particle 12, where these ratios can range from 4:1 (aqueous:oil) down to 1:10 (aqueous:oil).

In the microfluidic devices described above, the channel surfaces can be modified such that the aqueous phase is non-wetting, which can include a fluorination of the surface, or converting the surfaces to become hydrophobic or fluorophilic, either by a covalent silane-based treatment or another non-specific adsorption-based approach. Alternatively, a plastic polymer containing fluorophilic groups comprises the chip material and can be combined with the previously mentioned surface coatings or without a surface coating. Further, the oil used in some embodiments should be either a mineral oil (paraffin oil) supplemented with a non-ionic surfactant, vegetable oil supplemented with an ionic surfactant, or a fluorinated oil supplemented with a fluorinated surfactant (or any combination of these two oil/surfactant systems). These micro fluidic or millifluidic methods generate monodisperse (coefficient of variation less than 35%) populations of hydrogel particles 12 in rates equal to or exceeding 10 Hz, where collection is accomplished manually (by hand) or using automated fluidic handling systems. To prevent coalescence of hydrogel particles 12 prior to completion of the crosslinking reaction sufficient surfactant is necessary to stabilize the pre-gel droplets, however, high levels of surfactant also destabilize the droplet generation process. Therefore, a representative embodiment of the micro fluidic system for hydrogel particle 12 generation includes a low concentration of surfactant in the initial pinching oil flow (1% or less) that creates droplets followed by addition of an oil+surfactant solution from a separate inlet that is merged with the formed droplet and oil solution and contains a higher level of surfactant (up to 10 times or even 50 times higher than the initial surfactant).

In another alternative embodiment, the two oil pinching flows have the same concentration of surfactant. In still another embodiment, there is not a second pinching oil flow, and only the flow-focusing oil flow to generate droplets. Moreover, as explained above, in some alternative embodiments, there is no second pinching oil flow and only the t-junction oil flow is used to generate droplets. Of course, the t-junction droplet junction may optionally be combined with a second focusing oil inlet with equal or greater surfactant concentration.

After formation, hydrogel particles 12 are extracted from the oil phase using either centrifugation through an aqueous phase, or filtration through a solid membrane filtration device. For example, filtration may be used to reduce the volume of free aqueous solution holding the hydrogel particles 12 (free volume). In one embodiment, the aqueous free volume is less than about 35% of the total volume. In another embodiment, for generation of intentionally polydisperse populations, hydrogel particle generation is carried out in a milli- or micro fluidic platform, generating stocks of relatively monodisperse hydrogel particles 12 that are then mixed at desired ratios to obtain deterministic distributions and ratios of hydrogel particle 12 sizes. Ratios of hydrogel particle 12 sizes can be controlled precisely to control pore structure, or chemical properties in a final annealed scaffold 10 with stoichiometric ratios from: 1:1, 10:1, or exceeding 100:1.

Alternatively, generation of hydrogel particles 12 via a water-in-oil system can also be carried out using sonic mixing methods or a rotating vortex. These latter methods generate polydisperse populations of hydrogel particles 12 with size ranges from 100 nanometers to 500 micrometers. These particles can then be filtered using porous filters, microfluidic filtration, or other techniques known in the art to obtain a narrower size distribution of hydrogel particles 12 (e.g., coefficient of variation less than 50%). As another alternative, the component microgel particles 12 of different shapes can be fabricated using stop flow lithography, continuous flow lithography, and other methods to create shaped particles that rely on shaping flows (see Amini et al. International Publication No. W/2013/049404, which is incorporated by reference herein) combined with UV-initiated polymerization through a shape-defining mask. In this case the hydrogel particles 12 are non-spherical with long and short dimensions that can vary between 5 and 1000 micrometers. Shaped particles can also be fabricated by generating spherical particles in a water in oil emulsion, followed by extrusion of said particles through microfabricated constrictions that have length scales smaller than the diameter of the particle. The previously spherical particles adopt the shape of the constriction as they transition to a gel and retain that shape as they gel in the constriction by any of the crosslinker reactions listed above. The gels retain that shape after exiting the microfabricated construction. Shaped particles can allow for additional control of pores, overall porosity, tortuosity of pores, and improved adhesion within the final scaffold formed by hydrogel particle 12 annealing.

In one or more embodiments, the hydrogel particles 12 are either modified covalently or not (e.g., inclusion spatially within by diffusion) to provide biologically active molecules (e.g., small molecule drugs, antibiotics, peptides, proteins, steroids, matrix polymers, growth factors, antigens, antibodies, etc.). Inclusion of signaling molecules after formation of the hydrogel particle 12 may be accomplished through passive diffusion, surface immobilization (permanent or temporary), and/or bulk immobilization (permanent or temporary).

In another embodiment, nanoparticles are included in the initial pre-polymer solution and incorporated in the hydrogel particles 12 during initial polymerization or gelation, and the nanoparticles may include biologically active molecules for sustained or rapid release and delivery. In another embodiment, hydrogel particles 12 containing free primary amines (included as part of a lysine-containing oligopeptides) can be modified with NHS-Azide. To this set of hydrogel particles 12 can be added a protein modified with an NBS-phosphine, resulting in surface-coating of the micro gel particles 12 with the modified protein. FIG. 2E illustrates an embodiment in which a hydrogel particle 12 has nanoparticles 13 embedded therein.

Following the production and optional modification, the microgel particles 12 (which can be a homogeneous or heterogeneous mixture) may be applied to a desired location (in vitro, in situ, in vivo). The desired location on mammalian tissue can include, for example, a site of damaged tissue. The hydrogel particles 12 can be introduced alone in an aqueous isotonic saline solution or slurry (with preferably 30-99% volume fraction of hydrogel particles 12, and less preferably 1-30% volume fraction). Alternatively, hydrogel particles 12 can be introduced along with cells as single-cells or aggregates with cell to particle ratios from 10:1 to create dense cell networks within the final annealed scaffold 10 or 1:100 or even 1:1000 to create sparsely seeded scaffolds 10 with cells that produce factors useful for treatment. In another embodiment, hydrogel particles 12 can be cultured with cells at a low volume fraction of particles (<10%) for a period of time in cell-permissive media to promote adhesion to the individual hydrogel particles 12. These composite cell-adhered hydrogel particles 12 can be introduced as the active component that would anneal to form a microporous cell-seeded scaffold 10. Desired in vitro locations to introduce hydrogel particles 12 include well plates (e.g., 6-well, 96-well, 384-well) or microfluidic devices to form 3D microporous culture environments for cells following annealing, and enable subsequent biological assays or high-throughput screening assays with more physiologically-relevant 3D or multi-cellular conditions. For introduction in vitro, micro gel particle 12 solutions can be pipetted into wells or introduced via syringe injection followed by introduction of an annealing solution or triggering of annealing photochemically. Alternatively, a solution of microgel particle 12 solution could be mixed with a slow acting annealing solution (annealing occurring over 10-30 min) before delivery. In situ locations include treatment sites. Additionally, the micro gel particle solution can be applied to tissues through a catheter or cannula.

For introduction in situ micro gel particle containing solution can be stored separately from an annealing solution and be mixed during introduction (a method analogous to epoxy adhesives) to prevent premature initiation of the annealing reaction before entry into a treatment site.

In another, the two solutions could be stored in a syringe or squeeze-tube applicator with two barrels of equal or unequal diameters, such that when the plunger of the syringe is depressed or squeeze tube is compressed it simultaneously delivers both the hydrogel particles 12 and annealing solution at the correct stoichiometry. Alternatively, the two barrels can contain two separate hydrogel particle 12 types with annealing moieties that require the combination to initiate cross-linking. An alternative storage and delivery method would be in a single barrel syringe or a multi-use or single-use compressible tube in which the hydrogel particle slurry can be squeezed out to a desired volume and spread over the treatment site and then annealed through exposure to light, where the active agent for photochemistry is Eosin-Y at a concentration of 100 µM although concentrations within the range of 10 µM-1 mM will also work. Optionally, Eosin-Y is accompanied with a radical transfer agent which can be, for example, a chemical species with a free thiol group. An example of one such radical transfer agent includes cysteine or peptides including cysteine(s) described herein (e.g., used at a concentration of 500 µM). The light should be delivered via a wide spectrum white light (incandescent or LED), or a green or blue LED light. A flashlight, wand, lamp, or even ambient light may be used to supply the white light. Exposure should occur between 0.1 seconds and 1000 seconds, and the intensity of light should range between 0.01 mW/cm2 to 100 mW/cm2 at the site of annealing. In another embodiment, light-mediated annealing can be accomplished using a UV light (wavelengths between 300-450 nm), where the agent for photochemistry is either Lithium phenyl-2,4,6-trimethylbenzoylphosphinate (LAP) or IRGACURE® 2959, at a concentration of 0.01% w/v to 10% w/v. The exposure time should be between 0.1 seconds and 100 seconds, with a light intensity of 0.1 mW/cm2 to 100 mW/cm2 at a site of annealing. For embodiments in which light-initiated annealing is used, hydrogel precursors 12 would be stored in opaque (opaque with respect to wavelength range that initiates annealing) syringe or squeeze tubes containers prior to use. Desired in situ locations include internal tissue gaps or in cosmetic surgery applications to fill the tissue location and encourage tissue ingrowth and regeneration rather than the fibrotic processes common to contemporary injectables. Representative syringes or squeeze-tube applicators are disclosed in Griffin et al., U.S. patent application Ser. No. 15/179,151, published on Sep. 29, 2016 as U.S. Patent Application Publication No. 2016/0279283, herein incorporated by reference in its entirety.

An annealing process is initiated through the application of a stimulus (e.g., radical initiator, enzyme, Michael addition, etc.) or through interactions with a stimulus that is already present at the site of application of the hydrogel particles 12 that interacts with functional groups on the surface of the hydrogel particles 12, forming a solid contiguous highly porous scaffold 10 formed from the annealed (linked) hydrogel particles 12. If used in tissue, the annealing process can allow for fusion of the scaffold 10 to the surrounding tissue, providing an effective seal, a local medication and/or cell delivery device, a vascularized scaffold for in vivo sensing, and a better path to tissue treatment. The annealing process allows for on-site/on-demand gel formation (which is ideal for in vitro and in vivo applications), for example delivery through injection by a needle or through a catheter or cannula. The scaffold 10 may comprise of homogeneous or heterogeneous populations of micro gel particles 12. The heterogeneous populations of microgel particles 12 may vary in physical (e.g., in size, shape, or stiffness) or vary in chemical composition (e.g., varied ratios of linkers, varied annealing moieties, cell adhesive moieties, or loading of micro gels 12 with bioactive molecules or nanoparticles). The heterogeneous composition of the final annealed scaffold can be random or structured in layers of uniform composition to create gradients in micro-porous structures (by varying micro gel particle 12 sizes in layers, for example) or gradients of chemical composition (by layers of hydrogel particles 12 with different composition or bio-active molecule loading). Gradients may be useful in directing cell ingrowth in vivo, or development of tissue structures in vitro. Gradients in hydrogel particle 12 composition could be achieved by delivering sequential slurries of a gel of a single composition, followed by annealing, and then subsequent delivery of the next gel of a second composition, followed by annealing which links the new layer of micro gels to the previous layer, until a desired number of layers have been accumulated. Moreover, in some embodiments heterogenous particles can be intentionally mixed to achieve "islands" of heterogeneity. For example, a heparin compound can be unevenly distributed throughout the microporous hydrogel composition to thereby form heparin islands, comprising single or clustered groups of hydrogels, isolated within the microporous hydrogel composition. The thickness of each layer can be controlled using the volume of slurry injected and area of the injection site. An alternative embodiment to achieve gradients is to load a multi-barrel syringe applicator with different hydrogel compositions in each of the barrels. Each of the barrels are simultaneously compressed and feed to the nozzle in layered sheets. The nozzle itself of the syringe applicator can be non-circular or rectangular to create a layered slurry of multiple composition that is injected to a site in a ribbon-like structure, which can then be annealed in this arrangement. Formation of the structurally contiguous annealed scaffold 10 may be achieved through radical, enzymatic or chemical (e.g., Click chemistry) processes.

In one or more embodiments, annealing occurs through surface chemistry interactions between microgel particles 12 once they are ready to be placed at the delivery site. In one embodiment, the process occurs through radical-initiated annealing via surface polymerizable groups (e.g., radical initiation by photo-sensitive radical initiators, etc.). In another embodiment, the process occurs through enzymatic chemistry via surface presented enzymatically-active substrates. In another embodiment, the process occurs through covalent coupling via Michael and pseudo-Michael addition reactions. This method can use multiple hydrogel particle population types that when mixed form a solid or semi-solid scaffold 10 (e.g., micro gel particle 12 type A presenting, for example, nucleophilic surface groups and hydrogel particle 12 type B presenting, for example, $\alpha,\beta$-unsaturated carbonyl groups). In another embodiment, the process occurs through Click chemistry attachment. Similarly, this method can use heterogeneous hydrogel particle 12 populations that when mixed form a solid microporous gel. In another embodiment, annealing may be achieved using light (for example, either white light, LASER, or UV light) to initiate a chemical reaction between molecules on the gel surfaces, mediated by a light activated molecule in solution in and around (or directly covalently liked to) the microgels as described herein.

In one or more embodiments, hydrogel particles 12 are formed by a water-in-oil emulsion. Gelation of the hydrogel particles 12 occurs upon combination of bioinert polymer solution, e.g. PEG solution, with cross-linker solution (followed shortly by partitioning into microgel droplets before completion of gelation). A variety of substrates, including peptide ligands, can be further added for enhanced bioactivity. In one embodiment, scaffold formation is accomplished by addition and activation of radical photo-initiator to the purified hydrogel particles 12 to induce chemical cross-linking. In another embodiment, scaffold formation is accomplished by the use and/or activation of an endogenously present or exogenously applied enzyme to the purified hydrogel particles 12 that have been modified with two ligands either pre-formation, during formation, or post-formation to induce enzymatic cross-linking. In a separate embodiment, scaffold formation is accomplished using a combination of the aforementioned radical and enzymatic methods.

The resultant scaffold 10 of the presently disclosed subject matter provides a fully interconnected microporous scaffold in vivo. In general, porous scaffolds provide for greater access for live cells due to the freedom of movement through the pores (i.e., not requiring degradation to allow penetration like all current and previous non-porous and nano-porous scaffolds).

As disclosed herein, in some embodiments significant modifications have been made to known MAP hydrogels to change their chemical, structural and/or functional characteristics, which in turn render them suitable for applications not intended for the existing MAP hydrogels. Further details are provided in the Examples below.

In one embodiment, a MAP hydrogel was modified by adding a heparin to the hydrogel. By way of example and not limitation, a glycosaminoglycan heparin was added. The heparin can comprise a low molecular weight (LMW) to high molecular weight (HMW) heparin comprising variable molecular weights (MW 0.5 kDa to 50 kDa), including intentional mixtures thereof.

In some embodiments, MAP hydrogel formulations disclosed herein comprise a 4-arm PEG maleimide (MW about 10 kDa) reacted with 4-arm PEG thiol (MW about 10 kDa), with or without the inclusion of thiolated heparin (about 10% of repeat units modified with cysteamine; total concentration in gelling solution: 5 mg/mL). From this, controlled heterogeneous mixtures of heparin and non-heparin MAP hydrogel particles were created, as discussed further herein. In some formulations, the total PEG ranged from about 0.5-10 wt %, with added heparin ranging from about 0-200 mg/ml.

In some embodiments, MAP hydrogels provided herein allow for an unexpectedly large acceleration of annealing. To produce MAP hydrogel particles with accelerated annealing characteristics a custom synthesized 4-armed PEG (an approximately 1 to 2 arm maleimide functional group and an approximately 2 to 3 arms methacrylamide) was included during the gelation procedure to produce a hydrogel with a final concentration of methacrylamide of about 0.5 mM to about 1 mM. The resulting hydrogel formulation yielded full annealing in about 1/10 (or about 10%) the time of a MAP hydrogel without this additional group. That is, modified MAP hydrogel formulation resulted in an order of magnitude change in the time taken to reach full annealing. See Examples below.

In accordance with the present disclosure, there is also provided a pharmaceutical composition comprising a hydrogel solution, including in some aspects a MAP hydrogel, that further comprises heparin, a PEG, or a combination thereof. In one embodiment, the PEG is a custom synthesized 4-armed PEG as disclosed herein. There is also provided a method for administering the pharmaceutical composition comprising injecting or applying the pharmaceutical composition.

The present disclosure further provides a method for delivering one or more substances from the group comprising cells, fibroblasts, chondrocytes, osteogenic cells, stem cells, genes, drugs, proteins, chemicals, bioactive molecules, growth factors, and therapeutic proteins and peptides comprising administering the thermo-gelling solution as an injectable hydrogel of MAP particles for the delivery of these substances.

In one embodiment, the disclosure provides methods for administering novel delivery systems. In one aspect, the novel delivery systems are administered to treat injuries, diseases, disorders, and conditions in subjects in need thereof. In one aspect, the disclosed subject matter is useful for treating a musculoskeletal-associated injury, disease or disorder. Musculoskeletal-associated injuries, diseases or disorders are described herein or are known in the art. In one aspect, the method is useful for treating glotic incompetence, and/or laryngeal reconstruction.

In one embodiment, the present disclosure provides compositions and methods for tissue regeneration.

In one embodiment, one or more polymers can be used, for example, poly(lactic acid) (PLA), poly (l-lactic acid) (PLLA), polyglycolic acid (PGA), copolymers of PLA and PGA, polycaprolactone (PCL), poly(ethylene-co-vinyl acetate) (EVOH), poly(vinyl acetate) (PVA), polyethylene glycol (PEG), poly(glycerol sebacate) (PGS), poly(d,l-lactic-co-glycolic acid 50:50) (PLGA5050), poly(d-l-lactic-co-glycolic acid 85:15) (PLGA8515), polydioxanone (PDO), polyphosphazenes, polyurethane (PU) and modifications, analogs, and derivatives, thereof, polyhydroxybutyrates (PHB), poly-3-hydroxybutyrate (P3HB), poly-4-hydroxybutyrate (P4HB), polyhydroxyvalerate (PHV), polyhydroxyhexanoate (PHH), polyhydroxyoctanoate (PHO), poly(3-hydroxybutyrate-co-3-hydroxyvalerate) (PHBV), and poly (ethylene oxide) (PEO), as well as co-polymers, analogs, derivatives, modifications, and mixtures thereof.

Regarding modifications, for example, Poly (D, L-lactic-co-glycolic acid) (PLAGA) and poly(3-hydroxybutrate-co-3-hydroxyvalerate) (PHBV) are biodegradable and biocompatible polymers commonly used for tissue-engineered scaffolds. However, one can tailor the degradation rate of these polymers by altering the ratio of each component in the polymer composition, thereby rendering them suitable drug-release devices for both local and systemic delivery.

PLAGA is an FDA-approved copolymer of polylactide (PLA) and polyglycolide (PGA). PLA is a hydrophobic material with a degradation time greater than 24 months, which allows for great drug delivery potential. Through metabolic pathways, PLA degrades to lactic acid. PGA is a hydrophilic material and degrades at a faster rate, typically between 6 and 12 months, resulting in the glycolic acid byproduct. The polyester PLAGA degrades through hydrolysis and exhibits bulk degradation, releasing the non-toxic byproducts lactic acid and glycolic acid. Because of these acidic byproducts, local pH changes must be considered during PLAGA degradation. When used as a drug-delivery vehicle, variables such as molecular weight (Mw), copolymer composition, and crystallinity influence polymer degradation and the corresponding drug release kinetics.

PHBV is a polyester copolymer of hydroxybutyrate and hydroxyvalerate with adjustable processing and mechanical properties. By altering the copolymer composition and Mw, one can modify properties of PHBV, such glass transition temperature, crystallinity, and the rate of degradation. The accumulation of degradation products □-hydroxybutyric acid and hydroxyvaleric acid can thus be controlled.

One of ordinary skill in the art will appreciate that, based on the characteristics described herein, if a component can be used or modified and still achieve the desired characteristics and properties of the MAP hydrogel of the invention then it is encompassed by the invention.

Other implantable media and devices can be used to assist, or as supplements to, the use of hydrogels of the invention and substrates for delivery of the cells of the invention in vivo. These include, but are not limited to, sponges, such as those from Integra, fibrin gels, scaffolds formed from sintered microspheres of polylactic acid glycolic acid copolymers (PLAGA), and nanofibers formed from native collagen, as well as other proteins. The cells of the presently disclosed subject matter can be further combined with demineralized bone material, growth factors, nutrient factors, pharmaceuticals, calcium-containing compounds, anti-inflammatory agents, antimicrobial agents, or any other substance capable of expediting or facilitating bone growth.

In one aspect, the hydrogels of the present invention are useful for growing cells. In one aspect, they support the proliferation and differentiation of cells selected from the group comprising stem cells, pluripotent stem cells, committed stem cells, embryonic stem cells, adult stem cells, bone marrow stem cells, bone marrow-derived stem cells, adipose stem cells, umbilical cord stem cells, dura mater stem cells, precursor cells, differentiated cells, osteoblasts, myoblasts, neuroblasts, fibroblasts, glioblasts, germ cells, hepatocytes, chondrocytes, keratinocytes, smooth muscle cells, cardiac muscle cells, connective tissue cells, glial cells, epithelial cells, endothelial cells, hormone-secreting cells, cells of the immune system, normal cells, cancer cells, Schwann cells, and neurons.

Maintaining cells in culture refers to feeding with the appropriate growth medium when necessary, passaging the cells when necessary, etc.

Other materials may also be added to the hydrogels. Compounds and substances that can provide favorable matrix or mesh characteristics also include drugs and other substances that can produce a therapeutic or other physiological effect on cells and tissues within or surrounding an implant. Any substance may be used. Several preferred embodiments include use of any therapeutic molecule including, without limitation, any pharmaceutical or drug. Examples of pharmaceuticals include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfiram and disulfiram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor. All substances listed by the U.S. Pharmacopeia are also included within the substances of the present invention.

Other preferred embodiments involve the use of growth factors, including more than one growth factor, as described herein. In one embodiment, an effective amount of at least one growth factor, cytokine, hormone, or extracellular matrix compound or protein useful for enhancing wound healing is administered. In one aspect, a combination of these agents is used. In one aspect, growth factors useful in the practice of the invention include, but are not limited to, EGF, PDGF, GCSF, IL6, IL8, IL10, MCP1, MCP2, Tissue Factor, FGFb, KGF, VEGF, PLGF, MMP1, MMP9, TIMP1, TIMP2, TGFα, TGFβ, and HGF. One of ordinary skill in the art will appreciate that the choice of growth factor, cytokine, hormone, or extracellular matrix protein used will vary depending on criteria such as the type of injury, disease, or disorder being treated, the age, health, sex, and weight of the subject, etc. In one aspect, the growth factors, cytokines, hormones, and extracellular matrix compounds and proteins are human.

Proteins and other biologically active compounds that can be incorporated into, or included as an additive within, a composition comprising compounds of the present invention include, but are not limited to, hyaluronic acid, fluticasone, hedgehog pathway agonists, collagen (including cross-linked collagen), fibronectin, laminin, elastin (including cross-linked elastin), osteopontin, osteonectin, bone sialo-proteins (Bsp), alpha-2HS-glycoproteins, bone Gla-protein (Bgp), matrix Gla-protein, bone phosphoglycoprotein, bone phosphoprotein, bone proteoglycan, protolipids, bone morphogenetic protein, cartilage induction factor, skeletal growth factor, enzymes, or combinations and biologically active fragments thereof. Adjuvants that diminish an immune response can also be used in conjunction with the composite of the subject invention.

Other molecules useful as compounds or substances in the presently disclosed subject matter include, but are not limited to, growth hormones, leptin, leukemia inhibitory factor (LIF), tumor necrosis factor alpha and beta, endostatin, angiostatin, thrombospondin, osteogenic protein-1, bone morphogenetic proteins 2 and 7, osteonectin, somatomedin-like peptide, osteocalcin, interferon alpha, interferon alpha A, interferon beta, interferon gamma, interferon 1 alpha, and interleukins 2, 3, 4, 5 6, 7, 8, 9, 10, 11, 12, 13, 15, 16, 17 and 18. Embodiments involving amino acids, peptides, polypeptides, and proteins may include any type of such molecules of any size and complexity as well as combinations of such molecules.

Other useful materials and methods can be found in Griffin et al., U.S. patent application Ser. No. 15/179,151, published on Sep. 29, 2016 as Publication No. US 2016/0279283, and in Griffin et al., 2015, Nature Materials, 14:737-744, each of which is incorporated by their entirety herein.

Thus, using the disclosed compositions and therapeutics, methods are provided for treating tissues and subjects. For example, provided herein are methods of treating a tissue comprising, delivering to the tissue a non-degradable, non-immunogenic microporous hydrogel composition as disclosed herein, and activating an annealing initiator to thereby anneal the flowable hydrogel particles to form a covalently-stabilized scaffold of hydrogel particles. Exposing the non-degradable, non-immunogenic microporous hydrogel composition to an annealing initiator can comprise exposing the microporous hydrogel to a light source or a heat source. The composition can be administered by injection.

The tissue to be treated can be selected from epithelial tissue, skin tissue, dermal tissue, cardiac tissue, and gastrointestinal tissue. In some aspects, the tissue to be treated can comprise a laryngeal vocal fold, superficial lamina propria and/or vocalis muscle. The laryngeal vocal fold can be in a subject suffering from glottic incompetence and/or a subject in need of laryngeal reconstruction. In some aspects, the tissue to be treated can comprise a dermal tissue, wherein the non-degradable, non-immunogenic microporous hydrogel composition acts as a dermal filler.

In some aspects, delivering to the tissue can comprise a sub-epithelial injection under a scarring tissue, including for example vocal fold superficial lamina propria replacement in a scarred vocal fold. In some embodiments, the non-degradable, non-immunogenic microporous hydrogel composition can be configured to resist degradation in vivo for at least 90 days, preferably at least 180 days, most preferably indefinitely. Moreover, when administered, due to its low immunogenicity, less than about 40% of cells present within the microporous hydrogel composition following 6 months in vivo are immune cells. Still yet, administration of the microporous hydrogel composition with a heterogeneously distributed heparin compound can in some aspects cause increased tissue infiltration and vascularization with no substantial difference in immune response as compared to a microporous hydrogel composition without a heterogeneously distributed heparin compound.

In some embodiments, provided herein are methods of treating glottic incompetence, including providing a subject suffering from glottic incompetence and/or in need of laryngeal reconstruction, and administering a non-degradable, non-immunogenic microporous hydrogel composition disclosed herein to a laryngeal vocal fold and/or vocalis muscle, whereby the glottic incompetence in treated. This method can further comprise exposing the non-degradable, non-immunogenic microporous hydrogel composition to an annealing initiator to thereby anneal the flowable hydrogel particles to form a covalently-stabilized scaffold of hydrogel particles within the laryngeal vocal fold, superficial lamina propria, and/or vocalis muscle. The composition can be administered by injection. The composition can be configured to resist degradation in vivo for at least 90 days, preferably at least 180 days, most preferably indefinitely. In some aspects, the composition, with a heterogeneously distributed heparin compound, can cause increased tissue infiltration and vascularization with no substantial difference in immune response as compared to a microporous hydrogel composition without a heterogeneously distributed heparin compound.

EXAMPLES

The following Examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Experimental Approaches for Evaluating Map Hydrogel Compositions and Applications Thereof The role of the larynx in voice production is to convert aerodynamic energy from the chest and lungs into acoustic energy. Critical in this process is vocal fold adduction, which potentiates glottal valve closure. Glottic incompetence is a common laryngeal disorder that can cause dysphonia (loss of speech) and dysphagia (dysfunctional swallowing), which significantly diminishes an individual's quality of life. Causes of glottic incompetence include vocal fold atrophy, unilateral vocal fold paresis and paralysis, vocal fold scarring, and tissue loss due to surgery or radiation therapy.

Laryngeal reconstruction is the gold standard of care for moderate to severe glottic incompetence; however, this procedure is invasive and exposes patients to surgical complications. Several permanent materials such as Gore-Tex®, silastic, and titanium are used for laryngeal reconstruction; however, these materials require surgical implantation and fail to reproduce the physical properties of the surrounding tissue and can result in chronic inflammation, infection, implant migration, and extrusion. An alternative treatment to reconstructive surgery is medialization of the impaired vocal fold with injectable fillers (see FIGS. 1A and 1B). Medialization involves augmenting the size of the affected vocal fold, providing a medialized surface for the unaffected vocal fold to perform dynamic glottic functions of respiration, deglutition, and phonation. Injectable biomaterials (e.g. hyaluronic acid, collagen, etc.) have several advantages, including the ability to be quickly and non-invasively administered in an outpatient setting. Unfortunately, these materials are typically naturally derived and thus short-lived (due to the presence of degradative enzymes), typically lasting from several days to months. One of the most successful injectables is crosslinked hyaluronic acid, however this material begins to fail approximately 3-6 months after treatment. Synthetic injectable biomaterials have the potential for longer effects, but until recently, lacked good integration with host tissue without providing for duration-limiting degradative behavior (e.g. hydrolysis).

To address this need, a synthetic, injectable, and easy-to-apply product was tested. The results herein confirm that the disclosed compositions permanently restore vocal fold function and quickly affix through integration with the surrounding tissue.

MAP hydrogels are materials comprising microscale spherical building blocks with completely tunable physical and degradation properties. MAP gel shows excellent tissue integration that is independent of degradation or non-degradation due to interconnected microporosity. However, MAP was originally produced as a wound-healing scaffold with the intent of being resorbed by the body following healing. Therefore, several MAP parameters had to be engineered to meet the demands of permanently treating glottic incompetence.

MAP hydrogel was optimized to meet the physical parameters needed for effective treatment, including being non-resorbable and matching the physical characteristics of ex vivo vocal tissue (in some aspects using porcine vocal tissue as a model). MAP tissue integration was designed using chemotaxis for influencing cellular migration.

Currently, the initial treatment for patients with glottic incompetence is a simple injection treatment that lasts only several months. The limitation of the injectable treatment arises from both the use of naturally derived, degradable biomaterials and the lack of an engineered alternative. The MAP hydrogel compositions disclosed herein meet a clear need for an injectable and permanent treatment.

The MAP hydrogel compositions disclosed herein are highly tunable and achieve excellent tissue-biomaterial integration in vivo by combining seamless injectability with microporosity. In some aspects, pre-gel components include a PEG-maleimide backbone, PEG-thiol crosslinker and cell adhesive peptide (RGD, also referred to as Arginylglycylaspartic acid, the most common peptide motif responsible for cell adhesion to the extracellular matrix (ECM), found in species ranging from *Drosophila* to humans). Gel assembly advances via a Michael addition to form a highly crosslinked network (FIG. 1B). The MAP hydrogels were designed to use a building block approach to construct macroscale biomaterials with microscale building blocks made by water-in-oil microfluidic techniques to be both chemically and geometrically controllable (FIGS. 1B, 2B and 2C). Poly(ethylene glycol) (PEG)-based chemistry was used to take advantage of the high level of tissue integration, low immunogenicity, and its FDA Generally Regarded as Safe (GRAS) rating. Microfluidic techniques tightly control both particle chemistry and shape. The physical characteristics of the hydrogel are controlled upstream through the chemical make-up of the inlet solutions. The individual microgels can act as signal carriers by including the signal within the bulk of the hydrogel (not shown) or through encapsulation of nanoparticle carriers (FIGS. 2D and 2E).

MAP was optimized to meet the physical parameters needed for effective treatment, including matching the physical characteristics of ex vivo vocal tissue and being non-resorbable. To replicate the vocal aspects of the tissue the MAP gel macro-properties (e.g. stiffness) can in some embodiments be tuned accordingly.

The proper chemistry to match vocal fold tissue was determined using porcine cadaver larynges as control so that MAP hydrogels could be modified accordingly (macro-scale hydrogel properties accurately predict microgel properties). To provide a non-degradable scaffold, hydrolytically stable crosslinking chemistry using PEG backbone and PEG cross-linker were used (see FIG. 2B). Compressive stiffness (Young's modulus) characteristics were analyzed and matched to vocal fold tissue. The range of vocal fold stiffness desired was about 2 kPa to about 40 kPa, most preferably about 16 kPa.

Following production of the optimized MAP microgels, the maintenance of tissue function after MAP injection and scaffold formation was verified using ex vivo porcine larynges to evaluate the physical properties of injectables. Three porcine larynges were analyzed after injection augmentation of the right vocal fold with the MAP gel and the contralateral vocal fold serving as an internal control. The tissue was oscillated by heated and humidified airflow and imaged via high-speed camera. The goal was to retain vocal fold pliability and biomechanical vibratory characteristics. To analyze these properties, the laryngeal videostroboscopic parameters of amplitude, mucosal wave, and closure during simulated phonation following biomaterial injection were analyzed. Alterations in the biomechanical properties of vocal fold tissue produces disorganized vibratory patterns that can be quantified using laryngeal imaging techniques, ultimately correlating with poor voice quality in humans. Analysis of injection migration and tissue localization was quantified via gross examination and H&E analysis.

Material permanence and immunogenicity was tested using a subcutaneous murine model. Material permanence was validated using a modified small animal model for soft tissue filler characterization, including degradation, for four months (a time which shows significant degradation for hyaluronic acid-based materials). Immunogenicity was evaluated using immunofluorescent staining. Beyond glottic incompetence treatment, determining proper material properties for a permanent tissue filler will provide for additional applications (e.g. aesthetic dermal filler, and volumetric facial augmentation).

MAP hydrogels were further studied and optimized to provide enhanced tissue integration using chemotactic driving force for cellular migration. Enhancing tissue integration is vital for the treatment of glottic incompetence due to constant physical perturbation of the vocal fold area. If not properly integrated with the surrounding tissue, injectable biomaterials can become dislodged and "migrate" from the intended site of application. Unfortunately, subcutaneous injections of MAP gel typically achieve integration very slowly, resulting in about 1 mm of tissue penetration per month as indicated by significant collagen deposition between microgels. To overcome this a positive chemotactic gradient driving force was added to accelerate tissue integration within the MAP gel.

MAP microgels containing heparin (1 mg/mL) were infused with PDGF (10 µg/mL), a known chemoattractant for fibroblasts (the principle cell type of the vocal fold injection site). Different particle combinations (modified to unmodified microgels) were tested to optimize these chemotactic regions. This is a new approach to tissue-biomaterial integration and identification of gradient optimization. Immunofluorescent staining (nuclei and collagen) was used to evaluate integrated tissue to MAP constructs from a subcutaneous murine model to optimize proper spacing of PDGF-laden microgels to achieve accelerated integration (testing at Days 3, 7, and 14). Maximal integration of tissue with the MAP gel is optimal to prevent clinical migration after treating glottis incompetence. Microgradient-based enhancement of tissue integration will enhance the applications of the disclosed MAP hydrogels.

The enhanced MAP gel, with non-resorbable and improved integration abilities, was validated in a glottic incompetence leporine (rabbit) model. The ultimate test for any biomaterial used to treat glottic incompetence is the ability to maintain physical and geometric competence over time in a living system that will constantly place repetitive forces on the biomaterial. The leporine model is a cost-effective, validated, and reproducible animal model for vocal fold injection augmentation that allows for longitudinal study of these properties. This model allowed for confirmation that the MAP gel injection provides adequate tissue augmentation, while maintaining favorable vibratory biomechanical properties compared to the contralateral untreated vocal fold (internal control). A muscle simulator was used to deliver bipolar square wave pulses to each cricothyroid muscle, with heated and humidified air delivered through the glottis through a cuffed endotracheal tube. In the experimental groups, the left vocal fold served as the control and the right vocal fold had no stimulation, simulating vocal fold paralysis and producing glottic incompetence. The glottal incompetence was treated with injection of either saline (negative control), cross-linked hyaluronic acid (clinical standard), or the disclosed MAP gel compositions. The biomechanics of the phonation was recorded immediately following injection, at 6 weeks, 12 weeks, and 24 weeks. Specifically, the laryngeal vibratory characteristics of symmetry, amplitude, mucosal wave, and closure during phonation was be recorded at 5,000 frames per second using a high-speed camera (Photron SA3, Photron USA, Inc., San Diego, California, United States of America). Measurement of mucosal wave amplitude was defined as the difference between the maximum opening phase amplitude and maximum closed phase amplitude of vibration. Measurement of glottic opening was be defined as the open glottic area at the maximum closed phase. H&E staining of the harvested vocal folds quantified the amount of remaining injectable, extent of tissue integration, and identify any potential inflammatory response.

Example 2

Experiments to Modify Existing Map Hydrogels for Treatment of Glotic Incompetence and Other Conditions Disclosed herein is a MAP hydrogel composition. In some aspects, the disclosed MAP hydrogel is based on, and/or a modified version of, the MAP hydrogel disclosed in U.S. patent application Ser. No. 15/179,151, published on Sep. 29, 2016 as Publication No. US 2016/0279283 (hereinafter "the '151 patent application"; incorporated herein by reference in its entirety), and in Griffin et al., 2015, Nature Materials, 14:737-744 (hereinafter "Griffin et al."; incorporated herein by reference in its entirety). As disclosed herein, in some embodiments significant modifications have been made to the MAP hydrogel of the '151 patent application and Griffin et al. to changes its chemical, structural and/or functional characteristics, which in turn render it suitable for applications not intended for the existing MAP hydrogel.

In one embodiment, a MAP hydrogel was modified by adding a heparin to the hydrogel. By way of example and not limitation, a glycosaminoglycan heparin was added, as discussed further herein. The heparin can comprise a low molecular weight (LMW) to high molecular weight (HMW) heparin comprised of variable molecular weights (MW 0.5 kDa to 50 kDa), including intentional mixtures thereof.

Tests were conducted on hydrogel formulations with and without heparin added to the hydrogel. The tests included a hydrogel formulation comprising a 4-arm PEG maleimide (MW about 10 kDa) reacted with 4-arm PEG thiol (MW about 10 kDa), with or without the inclusion of thiolated heparin (about 10% of repeat units modified with cysteamine; total concentration in gelling solution: 5 mg/mL). The hydrogel particles were purified homogeneously (i.e., heparin and non-heparin hydrogel particles were kept separate during purification). Hydrogel particles were then combined ratiometrically to attain controlled heterogeneous mixtures of the heparin and non-heparin particles in the bulk of the produced scaffold. It was found that particle mixing can occur immediately prior or much earlier (e.g., months or years before). In some formulations, the total PEG ranged from about 0.5-10 wt %, with added heparin ranging from about 0-20 mg/ml.

Moreover, regarding non-resorbable scaffold data disclosed herein, data also indicates no loss of volume for the non-degradable formulation disclosed herein, with or without inclusion of 10% heparin gels.

An additional modification of MAP hydrogels, including the MAP hydrogels of the '151 patent application and Griffin et al., yielded unexpected and surprising benefits. More particularly, this modification caused an unexpectedly large acceleration of annealing. To produce MAP hydrogel particles with accelerated annealing characteristics a custom synthesized 4-armed PEG (an approximately 1 to 2 arm maleimide functional group and an approximately 2 to 3 arms methacrylamide) was included during the gelation procedure to produce a hydrogel with a final concentration of methacrylamide of about 0.5 mM to about 1 mM.

The resulting hydrogel formulation yielded full annealing in about $\frac{1}{10}$ (or about 10%) the time of a MAP hydrogel without this additional group. That is, modified MAP hydrogel formulation resulted in an order of magnitude change in the time taken to reach full annealing.

Example 3

Laryngeal Applications of Map Hydrogel

Figure 3A:
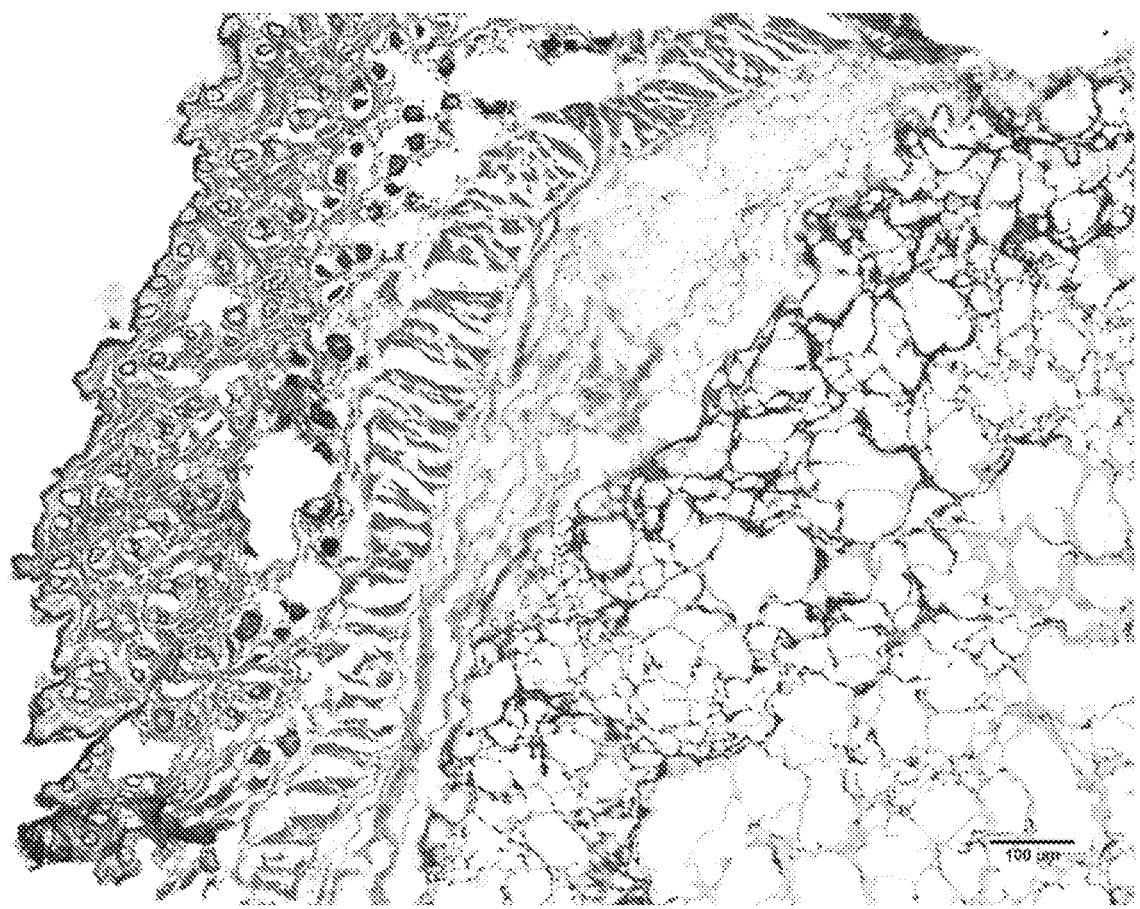
FIGS. 3A and 3B are a hematoxylin and eosin (H&E) stain and photograph, respectively, a hydrogel composition as disclosed herein in a mouse tissue.
Figure 3B:
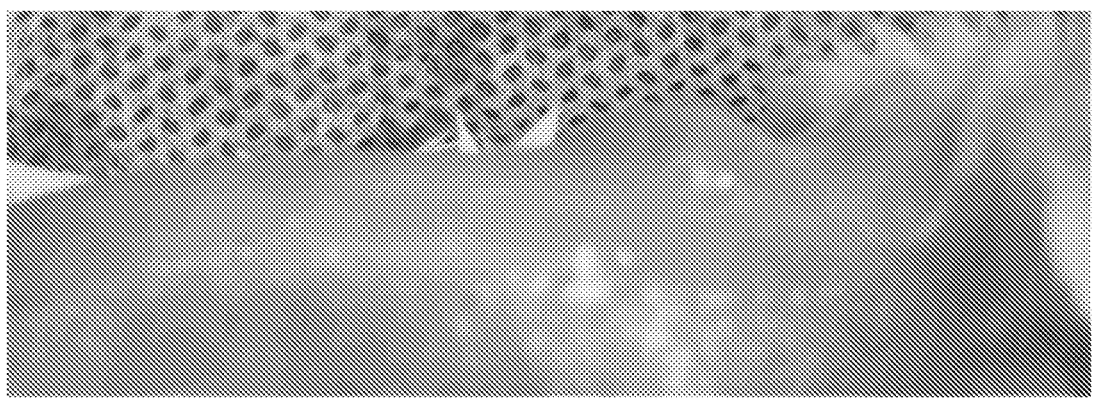

Two different chemistry formulations were developed to show the ability to tune the degradation properties. With a 4 arm PEG-MAL and PEG crosslinker (see FIG. 1B and FIG. 28) a gel was developed that showed permanence over a four (4)-month period in a mouse, as seen in the H&E stain and photograph of FIGS. 3A and 3B. A subcutaneous murine model demonstrated excellent volume retention with no significant loss of volume over 4-month trial (n=5). There was some swelling of the hydrogel because it wicks moisture from the tissue.

Figure 3C:
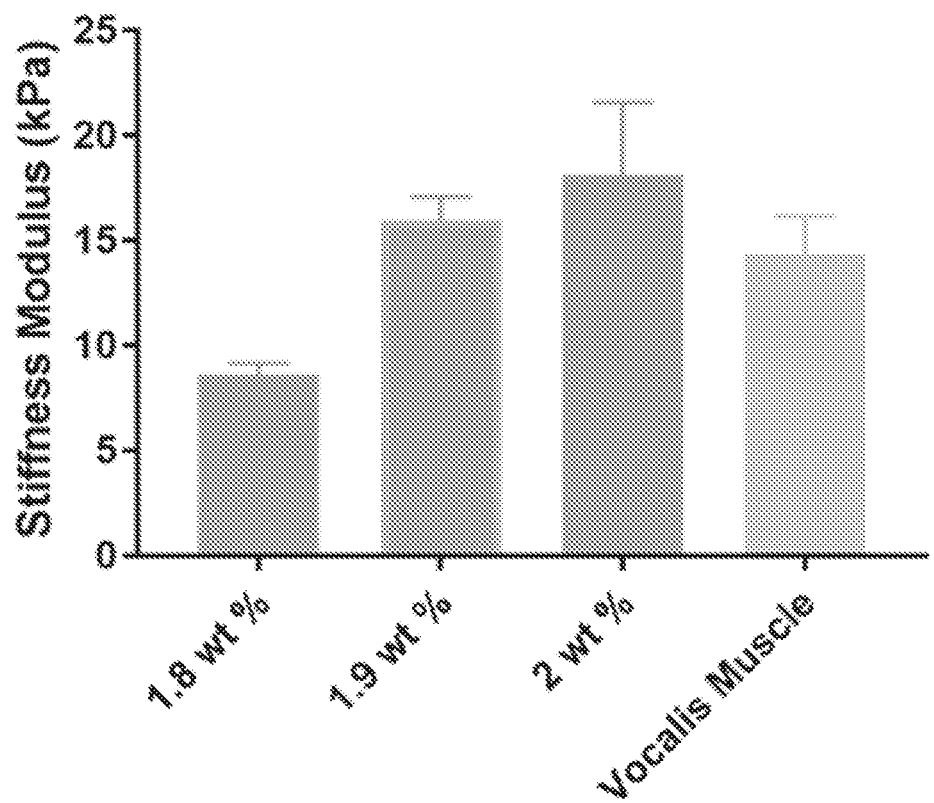
FIG. 3C is a histogram showing the results of stiffness testing of increasing concentrations of the disclosed hydrogel compositions.

During the initial materials development phase, the mechanical properties of the native porcine vocal fold were matched in order to properly restore vocal function. By changing the weight percent of the PEG-backbone in the hydrogel different stiffnesses can be achieved. Fresh entire pig vocal folds were used for the mechanical testing. All testing was done on an INSTRON® testing system (Norwood, Massachusetts, United States of America) equipped with a 5N static load cell. It was found that vocal folds were about 16 kPa and this corresponded to a 1.9% gel. See FIG. 3C.

Figure 4A:
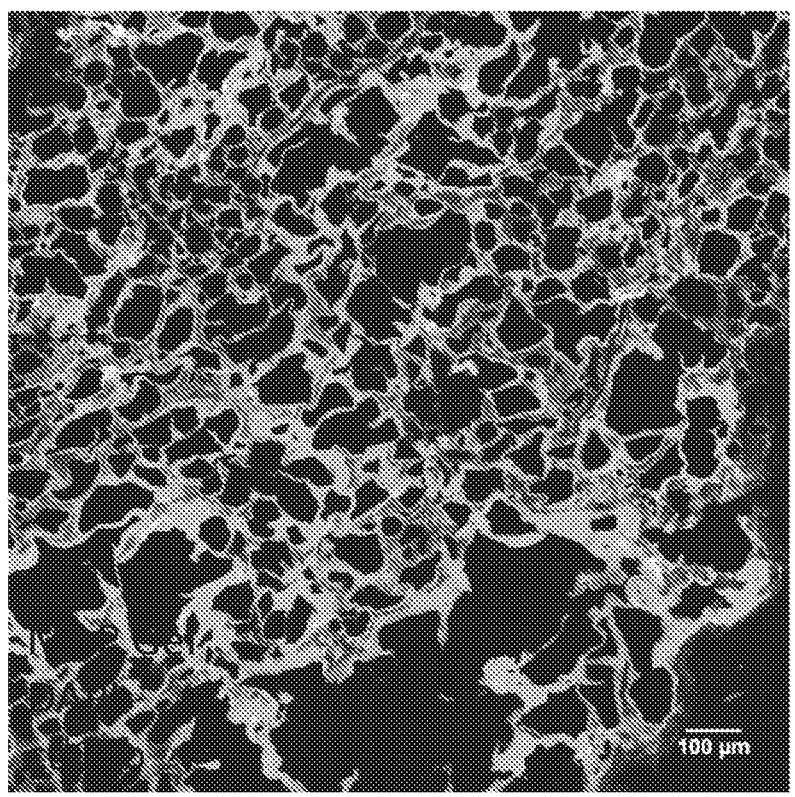
FIGS. 4A and 4B are images of tissues treated with the disclosed hydrogel compositions and showing low immune response.
Figure 4B:
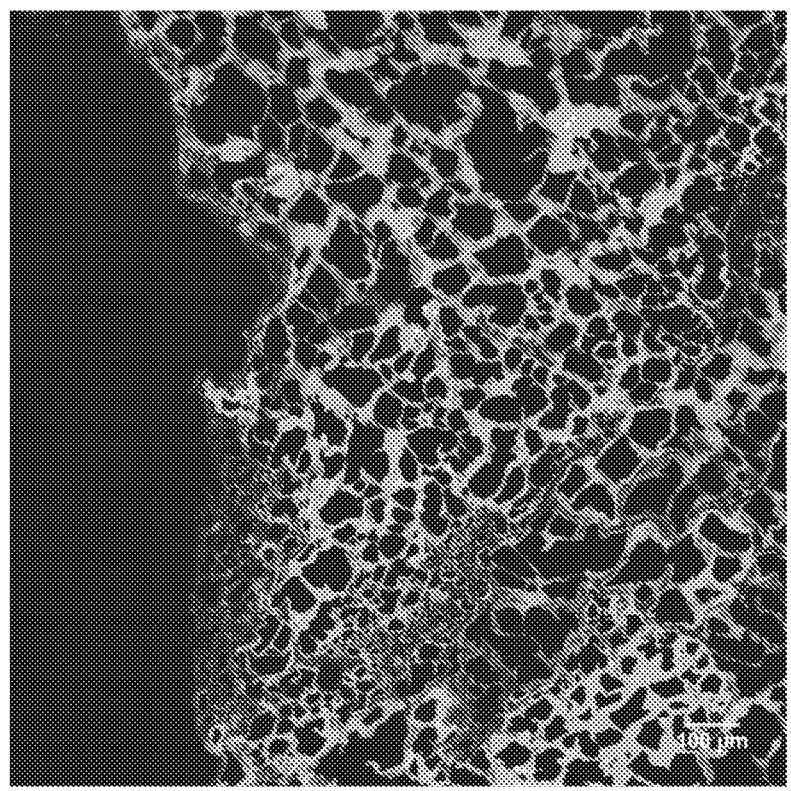

Referring to FIGS. 4A and 4B, immune cells were observed, but large bodies on the periphery of the gel, which would indicate a material mediated response, were not seen. The immune cells in the middle of the tissue shown in FIGS. 4A and 4B could be due to new tissue formation. Observed immune cells include fibroblasts to cd31; cells expressing CD11b, which is expressed on the surface of many leukocytes including monocytes, neutrophils, natural killer cells, granulocytes and macrophages; and cells expressing CD31, which is normally found on endothelial cells, platelets, macrophages and Kupffer cells, granulocytes, lymphocytes (T cells, B cells, and NK cells), megakaryocytes, and osteoclasts.

Figure 1B:
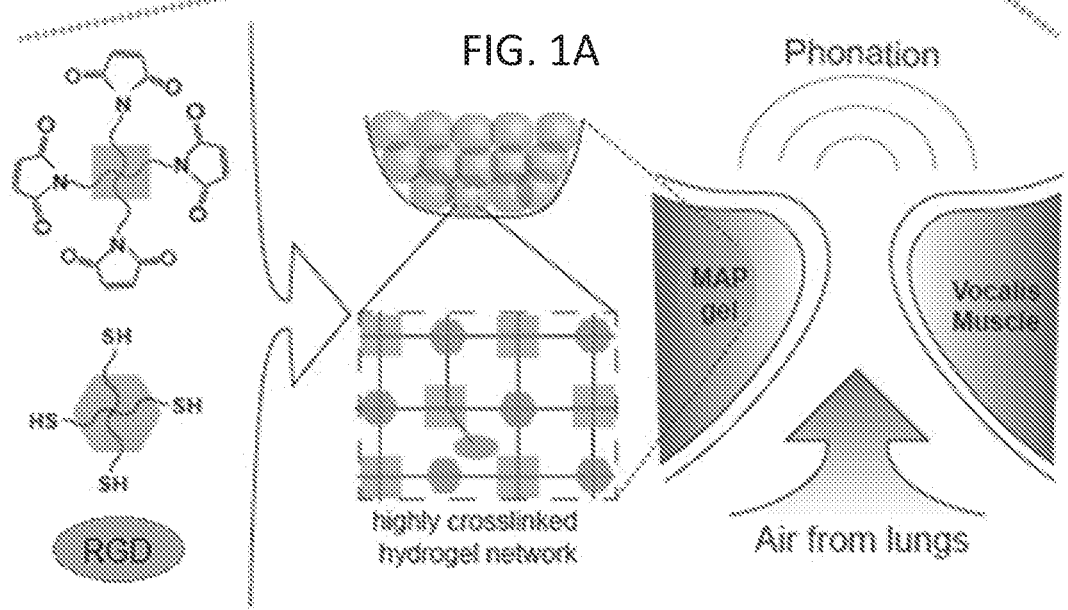
Figure 5D:
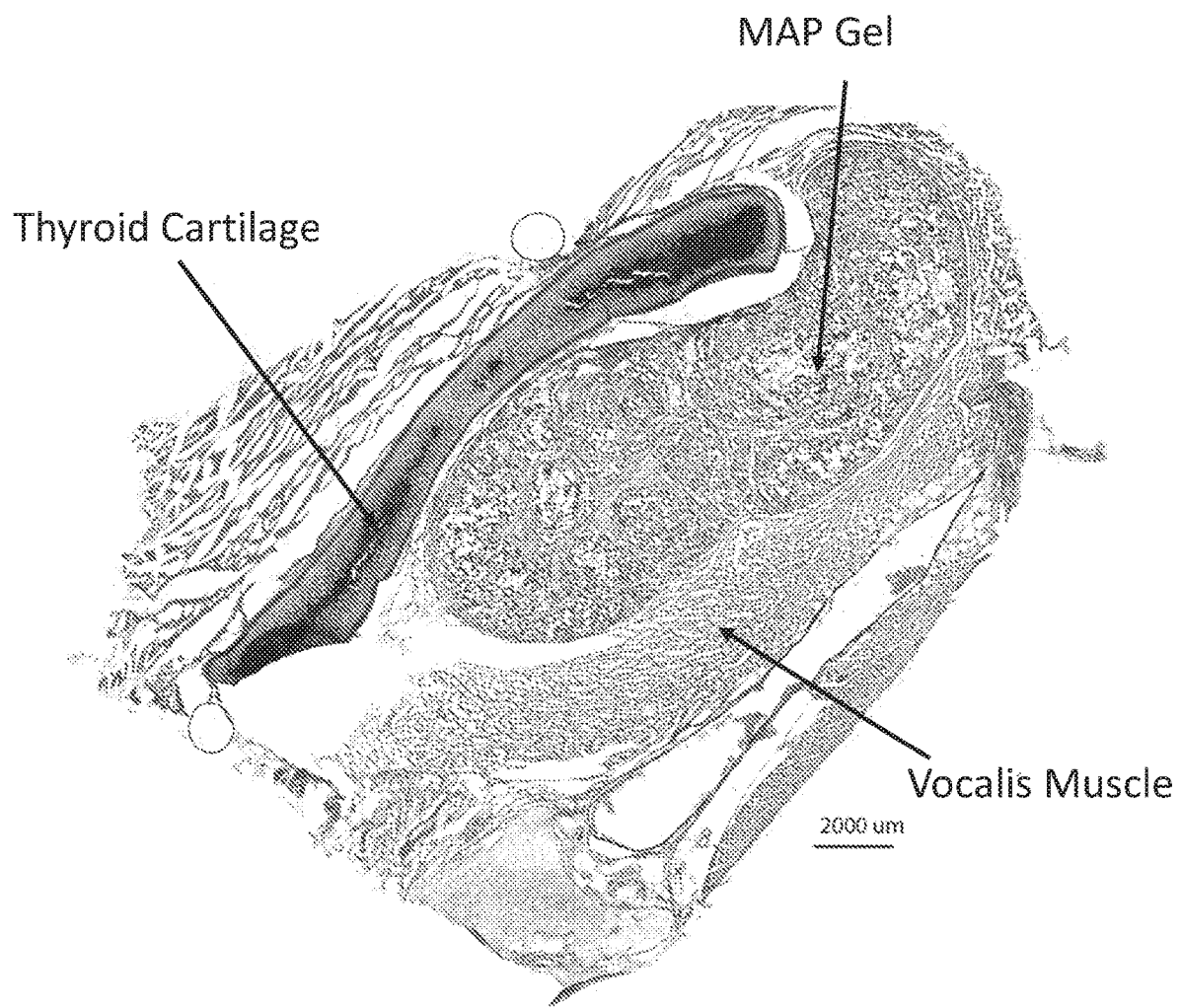
Figure 6A:
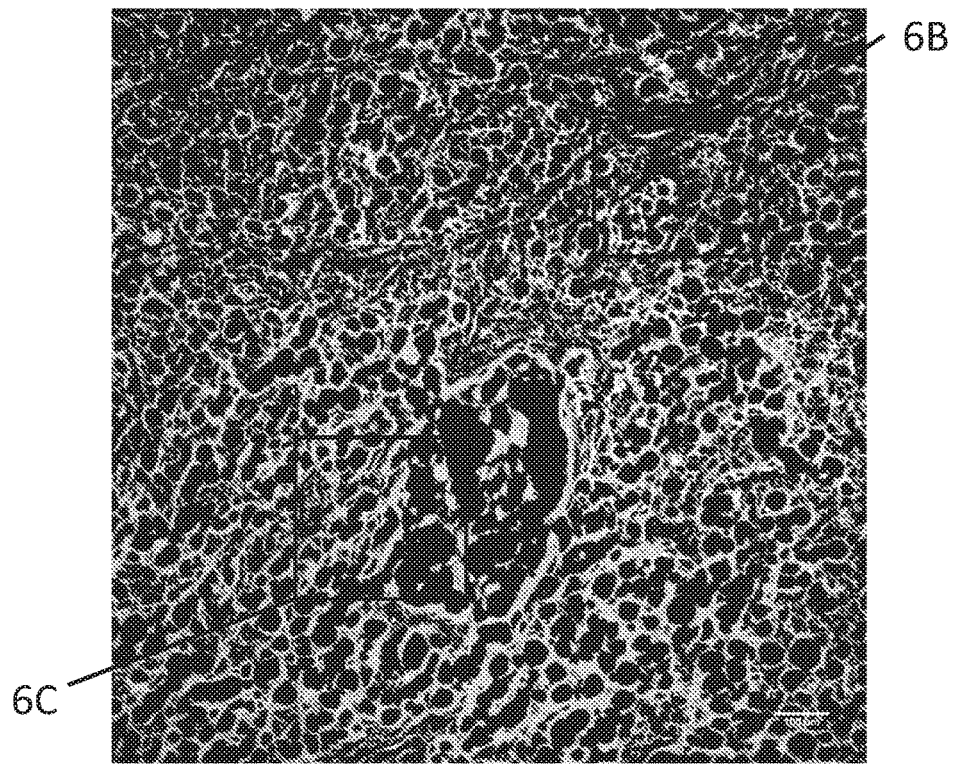
FIGS. 6A through 6E are electrophotographs of tissue treated with the disclosed hydrogel compositions and showing high integration and vascularization without high immune response.
Figure 6B:
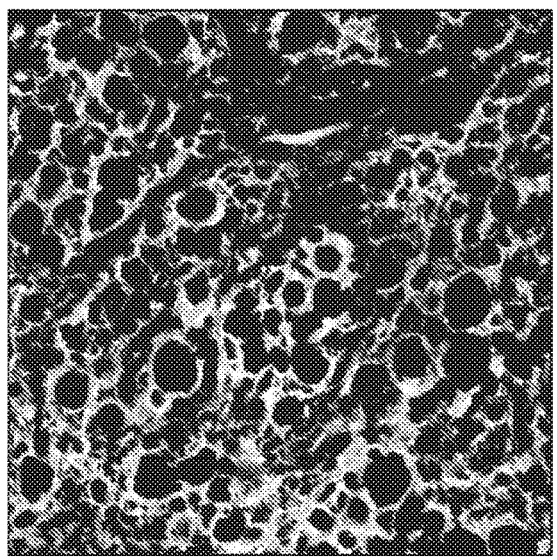
Figure 6C:
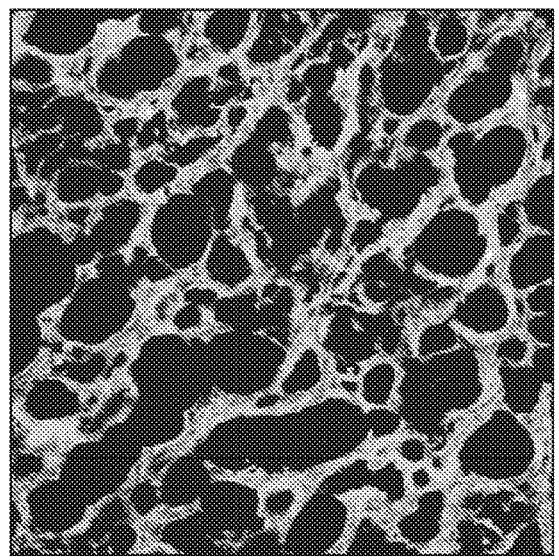
Figure 6D:
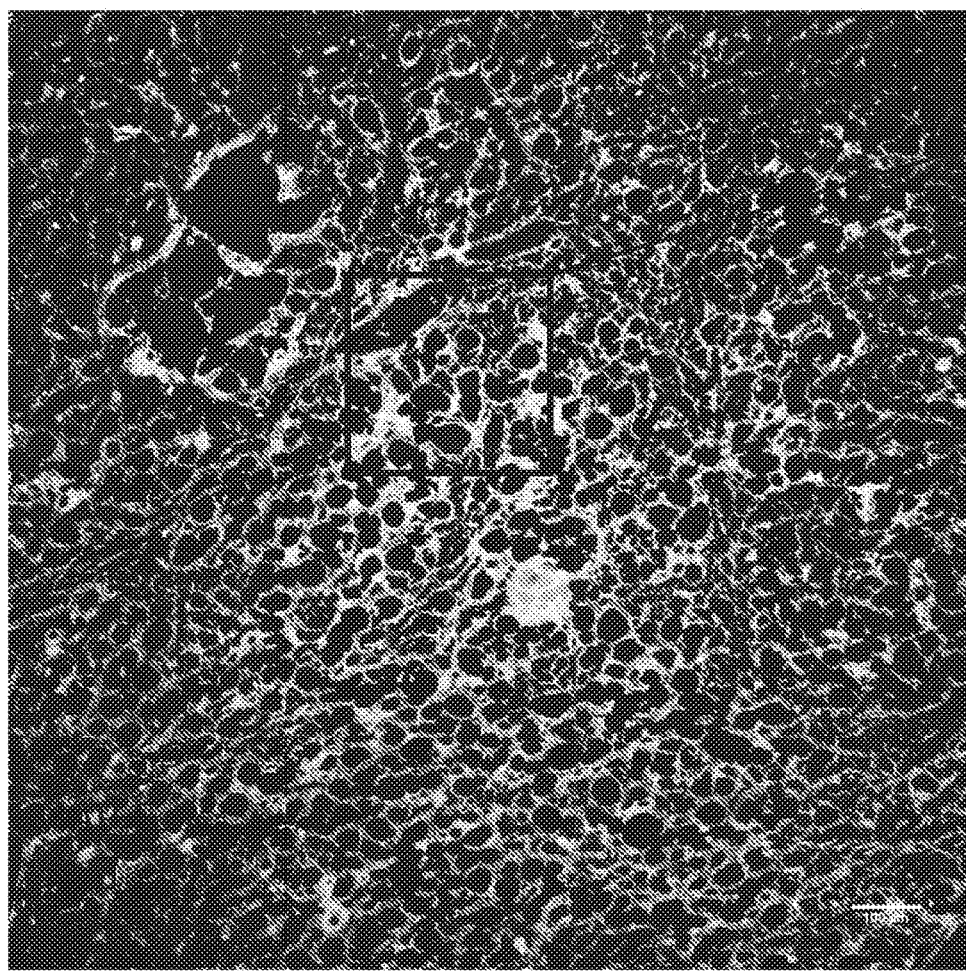
Figure 6E:
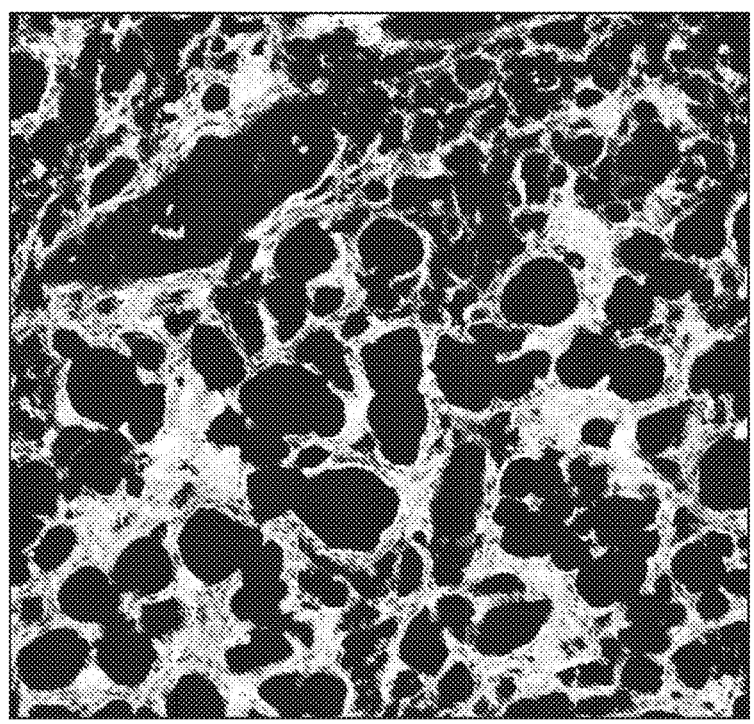

Referring to FIGS. 5A-5D, successful injection augmentation and annealing in a leporine (rabbit) model is shown (see FIG. 1A and FIG. 5A). These experiments involved the use of a 25-gauge (g) needle, an endoscopic camera, a light. Thus, human equipment was used in the rabbit model, which supports that the presently disclosed subject matter is clinically translatable. FIGS. 5B and 5C present an endoscopic view and FIG. 5D presents an H&E slide of the left hemilarynx. FIG. 1A shows similar results in a leporine model, both pre-medialization (left panel) and post-medialization (right panel). At one-month post injection, good medialization of the vocal fold was seen.

Histology shows there is good injection in the paraglottic space and intact mucosa overlying, as well as high integration without high immune response. Referring to FIGS. 6A-6E (showing endothelial cells beginning to form early vessels), one can observe how the tissue maps the pores but due to the processing the gel is collapsed good cell infiltration with low immune response was observed. In areas with high cell density, the exact identity of the cell could not be ascribed. In areas with low cell density, high levels of immune cells were seen, which is believed to be an indicator of new tissue development. No immune response on the exterior was seen, which is believed to indicate no material mediated immune response. Further, the exterior is most likely the frontier for the tissue coming in, but large groupings of cells or engulfment of the gels was not seen.

Additional cell determination is facilitated by a light degradable backbone which will allow us to collect cells and process by FACs. In current cell evaluations it believed that the majority are not cd11b or cd31 positive, but additional staining is employed to support these evaluations. It is hypothesized that the majority are fibroblasts and that there could be many benefits to high vascularity.

Figure 8A:
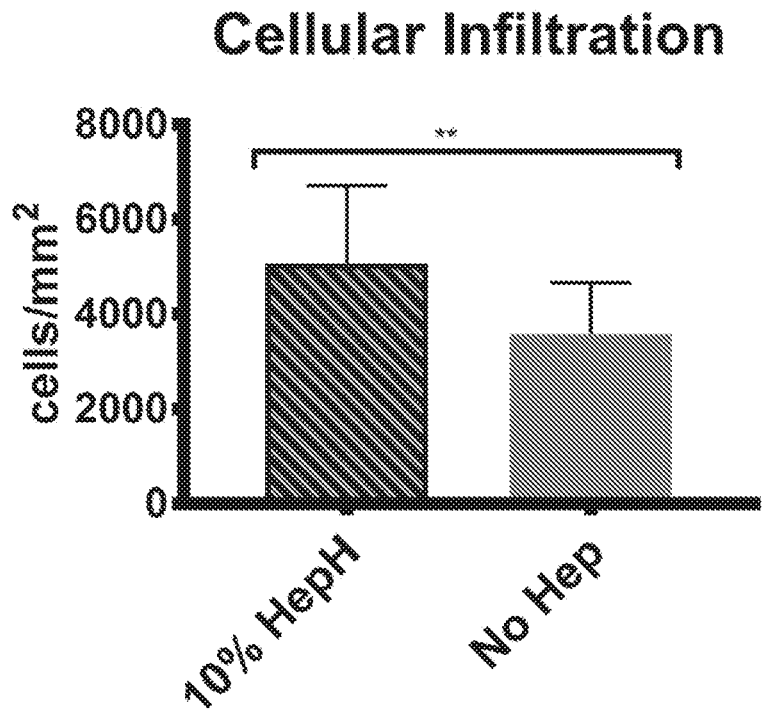
FIGS. 8A and 8B are histograms showing the results of treatment with the disclosed hydrogel compositions on cell infiltration (FIG. 8A) and platelet derived growth factor adsorption (FIG. 8B).
Figure 8B:
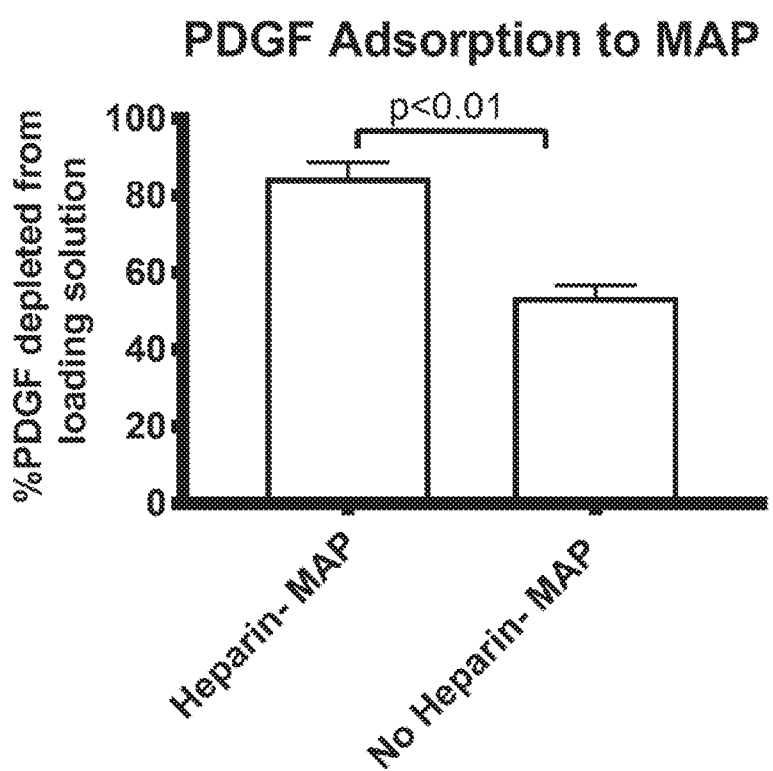

Heparin is a polysaccharide, more particularly an endogenous GAG produced by mast cells at sites of vascular injury. Heparin normally functions in wound repair and has anti-inflammatory properties and anti-coagulant properties in high doses by activating antithrombin. Heparin has a highly sulfated structure, with a strong negative charge, and demonstrates charge interactions with growth factors In heparin-MAP hydrogel assays, significantly increased cell infiltration was observed at 14 days. Increased platelet derived growth factor adsorption to heparin-MAP was also observed. IHC revealed no difference in immune response or vascularization. Referring to FIGS. 8A and 8B, heparin has tissue effects showing significantly increased cellular infiltration (p<0.01) after 14 days, no difference in immune response, and extensive vascularization. While it is not desired to be bound by any particular theory of operation, in vitro data showing increased PDGF adsorption to heparin—MAP provides a rationale for these results.

Example 4

Map Hydrogel Longevity, Inflammation, and Tissue Integration In Situ

The disclosed MAP hydrogels, being both non-degradable/non-resorbable and non-immunogenic, were tested for their permanence, inflammation and integration after an extended period of time post-injection.

Material permanence and immunogenicity was tested using a subcutaneous murine model. Material permanence was be validated using a modified small animal model for soft tissue filler characterization, including degradation, for four or more months (a time which shows significant degradation for hyaluronic acid-based materials). Immunogenicity was evaluated using immunofluorescent staining. Beyond glottic incompetence treatment, determining proper material properties for a permanent tissue filler provides for additional applications (e.g. aesthetic dermal filler and volumetric augmentation).

Figure 7A:
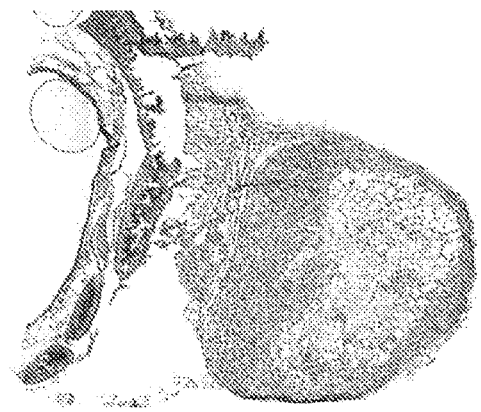
FIGS. 7A through 7D show results of treatment of tissues with the disclosed hydrogel compositions, wherein the imaging of FIG. 7A (H&E staining left panel, fluorescently-labeled MAP gel imaging right panel) shows good volume retention after 6 months post-injection, the imaging of FIG. 7B (H&E staining image left panel, with CD11b$^+$ imaging in inset) shows a negative immune response 6 months post-injection, FIG. 7C (CD11b$^+$ fluorescent imaging) shows minimal immune response and extensive cell infiltration 4 months (left panel) and 6 months (right panel) post-injection.
Figure 7A:
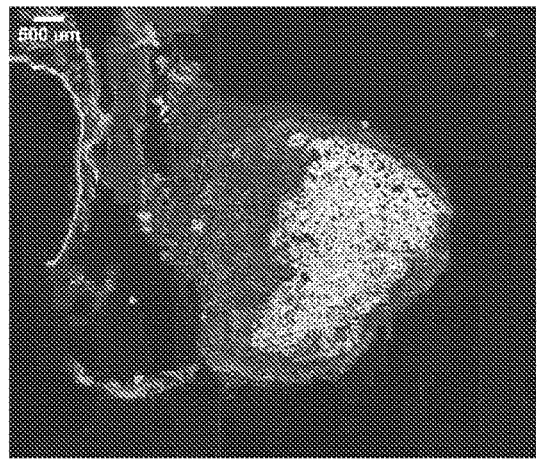
Figure 7B:
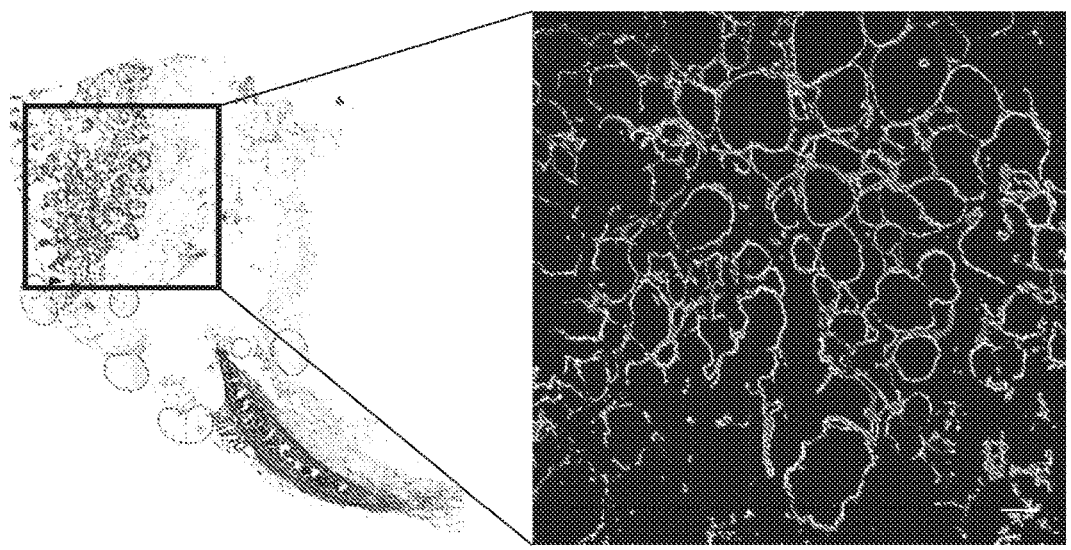
Figure 7C:
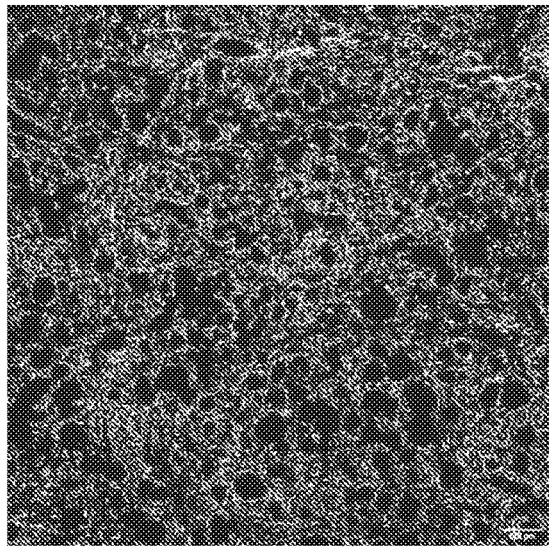
Figure 7C:
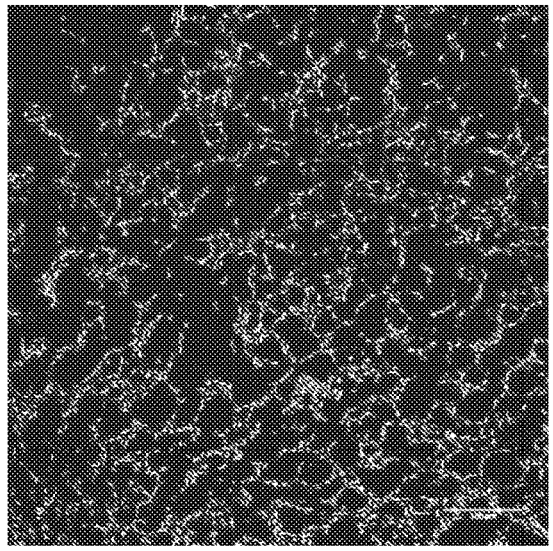
Figure 7D:
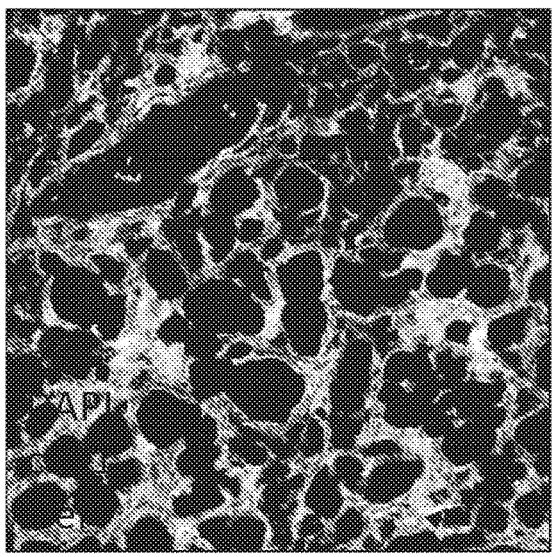
Figure 7D:
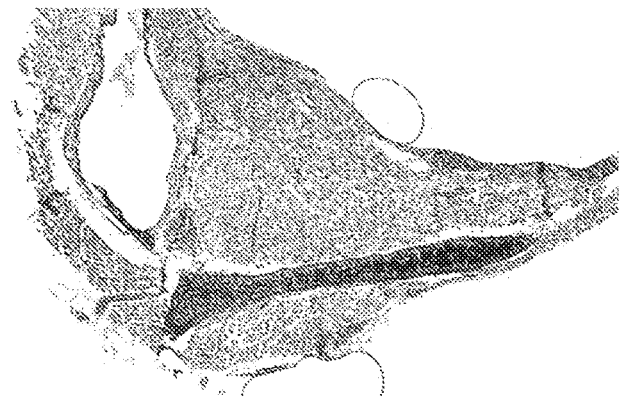

The imaging of FIG. 7A (H&E staining left panel, fluorescently-labeled MAP gel imaging right panel) shows good volume retention after 6 months post-injection. The imaging of FIG. 7B (H&E staining image left panel, with CD11b+ imaging in inset) shows a negative immune response 6 months post-injection. Likewise, using CD11b+ fluorescent imaging, FIG. 7C shows minimal immune response and extensive cell infiltration 4 months (left panel) and 6 months (right panel) post-injection. FIG. 7D shows early vascularization using CD31+ fluorescent imaging within the tissue only 6 weeks after injection (left panel; right panel is saline control at 6 months).

Example 5

Development of Treatment Protocols

Current Clinical Paradigm for Treatment. A variety of disease states can produce glottic incompetence including: vocal fold atrophy, paralysis, scar, and tissue loss from surgery or radiation. The most common cause, unilateral vocal fold paralysis, results from injury to the recurrent laryngeal nerve as a complication of thyroid or anterior cervical spine surgery, but can also be due to skullbase or chest surgery, infection, cancer, autoimmune disease, or trauma. Glottic incompetence from these conditions will result in varying degrees of a weak and breathy voice and difficulty swallowing liquids. Moderate to severe glottic incompetence can render a larynx completely dysfunctional, leaving an individual with a whisper-quiet voice and risk of aspiration during swallowing (sometimes requiring a feeding tube). This severity of glottic incompetence requires medialization of the affected vocal folds to restore laryngeal function.

Current Clinical Work Flow. Patients are referred to an Otolaryngologist by their primary care doctors or surgeons to diagnose the source of a voice or swallowing disorder, which may include glottic incompetence. The severity of the condition will determine the need for a laryngeal procedure such as in-office injection augmentation (a 15-minute office-based injection). Often the procedure will have to be repeated due to a lack of permanent injectables. Alternatively, a permanent laryngeal framework procedure, Type I laryngoplasty, can be offered if the condition is determined permanent. Permanent augmentation materials available for clinical use include silastic, Gore-Tex, titanium and calcium hydroxylapatite block. These permanent materials are surgically implanted into the vocal fold in the operating room. This procedure typically requires several hours and involves a neck incision, drilling a hole in the larynx to obtain access to the space below the vocal fold, and implantation of the selected material. Therefore, discussion between patients and their doctors considers one of two options: 1) a minimally invasive out-patient biomaterial injection (low expense, short recovery, poor long term success rate), and 2) an invasive surgery (high expense, long recovery, good long term success rate).

New treatment protocol. The disclosed hydrogel compositions provide a new treatment that overcomes the deficiencies in the existing treatment protocol. One approach is to use the current injectable treatment paradigm and substitute the current biomaterials for a permanent injectable option using the disclosed compositions. This seamless strategy will drive adoption significantly, as it does not require new skill development or philosophical treatment changes.

Patient Populations and Epidemiological Information. Unilateral vocal fold paralysis is most commonly iatrogenic as a result of a surgical procedure (46%) such as anterior cervical approaches to the spine, thyroid surgery, and carotid endarterectomy. However, 13% are due to malignancy and 18% are idiopathic in nature. The average age of this population is 60 years, with slightly increased incidence rate among women (58%). Vocal fold paralysis typically produces a characteristic "whisper" voice and choking on liquids during meals, which prompts examination of the larynx and assessment of vocal fold mobility. Additionally, voice disorders affect approximately 20% of the elderly population, which predominantly is a result of presbylarynges (aging larynx). With aging, the normal process of sarcopenia (muscle atrophy) progresses and this leads to a gap between the vocal folds resulting in poor voice quality, reduced vocal loudness, and increased vocal effort. This is an important quality of life issue in the elderly population, creating a barrier to communication and leading to further social isolation and depression.

REFERENCES

All references listed herein including but not limited to all patents, patent applications and publications thereof, scientific journal articles, and database entries are incorporated herein by reference in their entireties to the extent that they supplement, explain, provide a background for, or teach methodology, techniques, and/or compositions employed herein.

1. Kutty, J. K. & Webb, K. Tissue engineering therapies for the vocal fold lamina propria. Tissue Eng. Part B Rev. 15, 249-262 (2009).
2. Hertegård, S. et al. Cross-linked hyaluronan used as augmentation substance for treatment of glottal insufficiency: safety aspects and vocal fold function. The Laryngoscope 112, 2211-2219 (2002).
3. Hertegård, S. et al. Cross-linked hyaluronan versus collagen for injection treatment of glottal insufficiency: 2-year follow-up. Acta Otolaryngol. (Stockh.) 124, 1208-1214 (2004).
4. Griffin, D. R., Weaver, W. M., Scumpia, P. O., Di Carlo, D. & Segura, T. Accelerated wound healing by injectable microporous gel scaffolds assembled from annealed building blocks. Nat. Mater. 14, 737-744 (2015).
5. Sideris, E. et al. Particle Hydrogels Based on Hyaluronic Acid Building Blocks. ACS Biomater. Sci. Eng. (2016). doi:10.1021/acsbiomaterials.6b00444
6. Chan, R. W. & Rodriguez, M. L. A simple-shear rheometer for linear viscoelastic characterization of vocal fold tissues at phonatory frequencies. J. Acoust. Soc. Am. 124, 1207-1219 (2008).
7. Hillel, A. T. et al. Validation of a small animal model for soft tissue filler characterization. Dermatol. Surg. Off. Publ. Am. Soc. Dermatol. Surg. Al 38, 471-478 (2012).
8. Rosenthal L H1, Benninger M S, Deeb R H. Vocal fold immobility: a longitudinal analysis of etiology over 20 years. Laryngoscope. 2007 October; 117(10):1864-70.
9. Rosow D E. Trends in Utilization of Vocal Fold Injection Procedures.

Otolaryngol Head Neck Surg. 2015 November; 153(5):812-4.

10. Alipour F1, Finnegan E M, Jaiswal S. Phonatory characteristics of the excised human larynx in comparison to other species J Voice. 2013 July; 27(4):441-7. doi: 10.1016/j.jvoice.2013.03.013.
11. Dion G R1, Jeswani S1, Roof S1, Fritz M1, Coelho P G2, Sobieraj M2, Amin M R1, Branski R C3. Functional assessment of the ex vivo vocal folds through biomechanical testing: A review. Mater Sci Eng C Mater Biol Appl. 2016 Jul. 1; 64:444-453. doi: 10.1016j.msec.2016.04.018.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A non-degradable, non-immunogenic microporous hydrogel composition comprising:
   a collection of flowable hydrogel particles comprising a bioinert polymeric backbone;
   an annealing component comprising a physiologically-stable, radically polymerizable alkene, wherein the annealing component links the flowable hydrogel particles; and
   a heparin compound,
   wherein the microporous hydrogel composition is substantially non-degradable and substantially non-immunogenic and comprises a heterogenous mixture of hydrogel particles with a heparin compound and hydrogel particles without a heparin compound with a ratio of hydrogel particles with a heparin compound to hydrogel particles without a heparin compound selected from the group consisting of about 1:100, about 1:25, and about 1:10.

2. The non-degradable, non-immunogenic microporous hydrogel composition of claim 1, wherein the bioinert polymeric backbone comprises a poly(ethylene glycol) (PEG).

3. The non-degradable, non-immunogenic microporous hydrogel composition of claim 1, wherein physiologically-stable, radically polymerizable alkene comprises a methacrylamide.

4. The non-degradable, non-immunogenic microporous hydrogel composition of claim 1, wherein the heparin compound comprises a thiolated heparin, wherein a concentration of thiolated heparin is about 1 mg/ML to about 200 mg/mL.

5. The non-degradable, non-immunogenic microporous hydrogel composition of claim 1, wherein the heparin compound is unevenly distributed throughout the microporous hydrogel composition to thereby form heparin islands, comprising single or clustered groups of microgels, isolated within the microporous hydrogel composition.

6. The non-degradable, non-immunogenic microporous hydrogel composition of claim 1, wherein the heparin compound comprises a heparin having a molecular weight of about 15 kDa to about 25 kDa.

7. The non-degradable, non-immunogenic microporous hydrogel composition of claim 1, comprising a synthesized 4-armed PEG, wherein approximately 1 to 2 arms of the 4-armed PEG comprise a maleimide functional group, and wherein approximately 2 to 3 arms of the 4-armed PEG comprise a methacrylamide functional group.

8. The non-degradable, non-immunogenic microporous hydrogen composition of claim 7, comprising a concentration of hydrogel composition methacrylamide of about 0.5 mM to about 1 mM.

9. The non-degradable, non-immunogenic microporous hydrogel composition of claim 1, further comprising an annealing initiator, wherein activation of the annealing initiator causes annealing of the flowable hydrogel particles to form a scaffold of hydrogel particles having interstitial spaces therein, wherein the annealing initiator is activated by long wave ultra-violet (UV), visible, or infrared light.

10. The non-degradable, non-immunogenic microporous hydrogel composition of claim 1, wherein at least a portion of the flowable hydrogel particles further comprise a PEG crosslinker, wherein the amount of PEG in the composition ranges from about 0.5 wt % to about 10 wt %.

11. The non-degradable, non-immunogenic microporous hydrogel composition of claim 1, wherein the backbone polymer comprises a poly(ethylene glycol), hyaluronic acid, polyacrylamide, and/or polymethacrylate.

12. A method of treating a tissue comprising:
    delivering to the tissue a non-degradable, non-immunogenic microporous hydrogel composition of claim 1, wherein the non-degradable, non-immunogenic microporous hydrogel composition comprises an annealing initiator; and
    activating the annealing initiator to thereby anneal the flowable hydrogel particles to form a covalently-stabilized scaffold of hydrogel particles.

13. The method of claim 12, wherein activating the annealing initiator comprises exposing the microporous hydrogel composition to a light source or a heat source.

14. The method of claim 12, wherein the tissue to be treated is selected from epithelial tissue, skin tissue, dermal tissue, cardiac tissue, and gastrointestinal tissue.

15. The method of claim 14, wherein the tissue to be treated comprises a laryngeal vocal fold, superficial lamina propria and/or vocalis muscle.

16. The method of claim 12, wherein administration of the microporous hydrogel composition with a heterogeneously distributed heparin compound causes increased tissue infiltration and vascularization with no substantial difference in immune response as compared to a microporous hydrogel composition without a heterogeneously distributed heparin compound.

17. The method of claim 12, wherein the heparin compound is unevenly distributed throughout the microporous hydrogel composition to thereby form heparin islands within the microporous hydrogel composition.

18. The non-degradable, non-immunogenic microporous hydrogel composition of claim 1, comprising a heterogenous mixture of hydrogel particles with a heparin compound and hydrogel particles without a heparin compound, wherein the ratio of hydrogel particles with a heparin compound to hydrogel particles without a heparin compound is about 1:25.

19. The non-degradable, non-immunogenic microporous hydrogel composition of claim 1, comprising a heterogenous mixture of hydrogel particles with a heparin compound and hydrogel particles without a heparin compound, wherein the ratio of hydrogel particles with a heparin compound to hydrogel particles without a heparin compound is about 1:10.

* * * * *